United States Patent
Moyer et al.

(10) Patent No.: US 10,078,087 B2
(45) Date of Patent: *Sep. 18, 2018

(54) ASSAYS AND ENHANCERS OF THE HUMAN DELTA ENAC SODIUM CHANNEL

(75) Inventors: Bryan Moyer, San Deigo, CA (US); Min Lu, San Diego, CA (US); Fernando Echeverri, Chula Vista, CA (US); Hong Chang, San Diego, CA (US)

(73) Assignee: SENOMYX, INC., San Diego, CA (US)

(*) Notice: Subject to any disclaimer, the term of this patent is extended or adjusted under 35 U.S.C. 154(b) by 1399 days.

This patent is subject to a terminal disclaimer.

(21) Appl. No.: 12/278,064

(22) PCT Filed: Jan. 26, 2007

(86) PCT No.: PCT/US2007/002293
§ 371 (c)(1),
(2), (4) Date: May 18, 2009

(87) PCT Pub. No.: WO2007/092185
PCT Pub. Date: Aug. 16, 2007

(65) Prior Publication Data
US 2010/0009385 A1      Jan. 14, 2010

Related U.S. Application Data

(63) Continuation-in-part of application No. 10/563,758, filed as application No. PCT/US2004/021853 on Jul.
(Continued)

(51) Int. Cl.
G01N 33/68 (2006.01)
G01N 33/02 (2006.01)
G01N 33/14 (2006.01)

(52) U.S. Cl.
CPC ......... *G01N 33/6872* (2013.01); *G01N 33/02* (2013.01); *G01N 33/14* (2013.01)

(58) Field of Classification Search
CPC ............ A23V 2002/00; A23V 2200/15; A23V 2200/16; A23V 2300/00; A23L 1/2209;
(Continued)

(56) References Cited

U.S. PATENT DOCUMENTS 5,693,756 A    12/1997 Li et al.
6,083,986 A    7/2000 Castle et al.
(Continued)

FOREIGN PATENT DOCUMENTS

WO    02/087306       11/2002
WO    WO 2005015158   * 2/2005
WO    WO 2007146120   12/2007

OTHER PUBLICATIONS

Birch et al., (Drugs Discovery Today. May 2004. vol. 9:410-418).*
(Continued)

*Primary Examiner* — Jana A Hines
(74) *Attorney, Agent, or Firm* — Robin L. Teskin; LeClairRyan PLLC

(57) ABSTRACT

This invention relates to electrophysiological assays that measure sodium conductance activity of a delta human epithelial sodium channel (ENaC) in the presence and absence of delta hENaC enhancers. Also, the invention generally relates to assays for identifying compounds that enhance the activity of delta hENaC, especially in an oocyte expression system. These compounds have potential application in modulating (enhancing) salty taste perception.

31 Claims, 4 Drawing Sheets

Specification includes a Sequence Listing.

Related U.S. Application Data 9, 2004, said application No. 10/563,758 is a continuation-in-part of application No. 10/133,573, filed on Apr. 29, 2002, now abandoned.

(60) Provisional application No. 60/764,353, filed on Feb. 2, 2006, provisional application No. 60/287,413, filed on May 1, 2001, provisional application No. 60/485,745, filed on Jul. 10, 2003.

(58) Field of Classification Search
CPC .... A23L 1/237; C07K 14/705; G01N 33/566; G01N 33/5044; G01N 33/5064; G01N 2500/10; G01N 2333/726
See application file for complete search history.

(56) References Cited

U.S. PATENT DOCUMENTS

| | | |
|---|---|---|
| 6,287,859 B1 | 9/2001 | DeWeille et al. |
| 6,524,798 B1 | 2/2003 | Goldbard et al. |
| 2002/0128203 A1 | 9/2002 | Schild et al. |
| 2002/0168625 A1 | 11/2002 | Weaver |
| 2004/0072254 A1* | 4/2004 | Callamaras .......... C07K 14/705 435/7.2 |
| 2005/0037369 A1 | 2/2005 | Neote et al. |
| 2005/0059094 A1 | 3/2005 | Servant et al. |
| 2005/0177886 A1 | 8/2005 | Margolskee et al. |
| 2006/0089306 A1 | 4/2006 | Wallace et al. |
| 2006/0223117 A1 | 10/2006 | Moyer et al. |
| 2007/0071757 A1 | 3/2007 | Yu et al. |
| 2009/0253159 A1 | 10/2009 | Maher et al. |

OTHER PUBLICATIONS

Birch et al Drug Discovery Today. May 2004/ vol. 9:410-418.*
Denyer et al., DDT, vol. 3, 1998, pp. 323-332.
Qi et al., JBC, vol. 274, 1999, pp. 30345-30348.
McDonald et al, Amer. J. Physiol., vol. 268, 1995, C1157-C1163.
Waldmann et al., Molecular Cloning and Functional Expression of a Novel Amiloride-sensitive Na+ Channel. (2005) Journal of Biological Chemistry. Volume 270, No. 46, pp. 27411-27414.
Mick VE, et al. "The alpha-subunit of the epithelial sodium channel is an aldosterone-induced transcript in mammalian collecting ducts, and this transcriptional response is mediated via distinct cis-elements in the 5'-flanking region of the gene," Mol Endocrinol. Apr. 2001;15(4):575-88.
Ishikawa T, et al. "Electrophysiological characterization of the rat epithelial Na+ channel (rENaC) expressed in MDCK cells. Effects of Na+ and Ca2+," J Gen Physiol. 1998 Jun;111(6):825-46.
Li XJ, et al. "Alternatively spliced forms of the alpha subunit of the epithelial sodium channel: distinct sites for amiloride binding and channel pore," Mol Pharmacol. Jun. 1995;47(6):1133-40. [Abstract Only, 4 pages].
González JE, et al. "Cell-based assays and instrumentation for screening ion-channel targets," Drug Discov Today. Sep. 1999;4(9):431-439.

* cited by examiner

αβγ ENaC Activation = 285 +/- 77%

δβγ ENaC Activation = 298 +/- 46%

ASSAYS AND ENHANCERS OF THE HUMAN DELTA ENAC SODIUM CHANNEL

RELATED APPLICATIONS

This application claims benefit of priority to and incorporates by reference in its entirety International Application No. PCT/US2007/002293 filed on Jan. 26, 2007, which claims priority to U.S. Provisional Application No. 60/764,353 filed on Feb. 2, 2006.

SEQUENCE LISTING

The sequence listing in the file named "43268o1602.txt" having a size of 41,596 bytes that was created Feb. 2, 2017 is hereby incorporated by reference in its entirety.

FIELD OF THE INVENTION

This invention relates to electrophysiological assays that identify compounds that modulate a human sodium epithelial channel comprised of delta, beta and gamma subunits in the presence and absence of ENaC enhancers and the use thereof to modulate human salty taste perception. The invention more specifically relates to the identification of compounds that enhance a human ENaC comprised of delta, beta and gamma subunits expressed in an oocyte expression system. Further the invention relates to assays for identifying compounds that modulate a human ENaC comprised of delta, beta and gamma subunits and the use thereof to modulate human salty taste perception.

As described herein electrophysiological assays conducted using human ENaC comprised of either alpha, beta and gamma subunits or delta, beta and gamma subunits have shown that amiloride blocks delta beta gamma ENaC, ~25-fold less efficiently than alpha beta gamma ENaC. Unlike other mammals, amiloride only slightly reduces the intensity of sodium chloride taste, i.e., by about 15-20% when used at concentrations that specifically modulate ENaC function. Experiments conducted by the inventors have shown that amiloride did not elicit a significant effect on perceived salt intensity when tested at levels ~300-fold above IC50 values for alpha beta gamma ENaC in oocytes (equivalent to only ~10-fold over IC50 values for delta beta gamma ENaC in oocytes).

Based thereon, assays have been developed which are disclosed herein to identify compounds that modulate the delta beta gamma human ENaC since it is anticipated that these compounds will potentially modulate human salty taste perception.

BACKGROUND OF THE INVENTION

Epithelial sodium channels (ENaC) are members of the ENaC/degenerin family of ion channels that includes acid-sensing ion channels (ASIC) in mammals, mechanosensitive degenerin channels in worms, and FMRF-amide peptide-gated channels in mollusks (Kellenger, S. and Schild, L. (2002) Physiol. Rev. 82:735-767). ENaC mediates apical membrane Na$^+$ transport across high resistance epithelia in numerous tissues including kidney, colon, and lung.

ENaC is known to be a heterotrimeric channel comprised of α, β, and γ subunits. This heterotrimeric channel has been hypothesized to be involved in human salty taste perception. Additionally, this channel is involved in the maintenance of extracellular volume and blood pressure, absorption of fluid from the lungs during late stages of gestation, and transduction of salt taste. (See e.g., Rossier, B. C. et al., Annu. Rev. Physiol. 62:877-897 (2002); Alvaraz et al. Annu. Rev. Physiol. 62:573-594 (2000); and Bigiani et al., Prog. Biophys. Mol. Biol. 83:193-225 (2003)).

For example, it is known that mutations in the human ENaC (hENaC), particularly gain of function mutations result in hypertension due to increased renal Na$^+$ reabsorption in Liddle's syndrome (Schild et al., Proc. Natl. Acad. Sci., USA 92:5699-5703 (1995); Shimkets et al., Cell 79:407414 (1994); and Snyder et al., Cell 83:969-98 (1995)). By contrast, it is known that hENaC loss of function mutations result in salt-wasting due to decreased renal Na$^+$ reabsorption in pseudohypoaldosteronism type I (PHA1). (See Grunder et al., EMBO. J. 16:899-907 (1997); and Chang et al., Nat. Genet. 12:248-253 (1996)). The clinical symptoms of salt-wasting include by way of example hyponatremia, hyperkalemia, dehydration, elevated serum aldosterone, and mineralocorticoid unresponsiveness.

BRIEF DESCRIPTION AND OBJECTS OF THE INVENTION

In this invention disclosure we describe screening assays to identify human delta epithelial sodium channel (ENaC) enhancers.

It is a specific object of the invention to provide electrophysiological assays that measure sodium conductance of delta beta gamma human ENaC channels in the presence and absence of delta ENaC enhancers.

It is another specific object of the invention to provide enhancers of the delta beta gamma human ENaC channels in an oocyte expression system.

It is another object of the invention to identify delta ENaC specific enhancers that modulate, preferably enhance human salty taste perception.

More preferably it is an object of the invention to provide patch clamping or two electrode voltage clamping assays using oocytes that express a human delta beta gamma ENaC channel for identifying compounds that modulate the activity of this channel.

As described infra, experiments performed by the inventors have not demonstrated a significant effect of amiloride on perceived salt intensity when tested at levels ~300-fold above the IC50 value for alpha beta gamma ENaC in oocytes (equivalent to ~10-fold over the IC50 value for delta beta gamma ENaC in oocytes). Since delta ENaC is ~25-fold less sensitive to amiloride than alpha ENaC, and human salt taste is poorly inhibited by amiloride, it is believed that human salt taste may be mediated, in part, by a delta ENaC-based sodium channel. Thus, the invention provides assays for identifying modulators of the human delta channel which may be comprised of a delta beta gamma heterotrimer, a delta only monomer, or any combination of delta with beta and gamma or other protein subunits. The compounds identified and their derivatives potentially can be used as modulators of human salty taste in foods, beverages and medicinals for human consumption.

BRIEF DESCRIPTION OF THE FIGURES

FIG. 1A: representative amiloride inhibition curves for αβγ hENaC (n=16) and δβγ hENaC (n=10). Half-maximal inhibition of δβγ hENaC required ~25-fold higher concentrations of amiloride compared with αβγ hENaC and αβγ mENaC. FIG. 1B: representative 6363969 dose-response curves for αβγ hENaC (n=46) and δβγ hENaC (n=11). 6363969 activated δβγ hENaC with similar efficacy and potency as αβγ hENaC. Experiments with δβγ hENaC used 10 uM amiloride whereas experiments with αβδ hENaC used 1 uM amiloride, concentrations yielding >90% hENaC inhibition, to calculate % hENaC activation values.

SUMMARY OF INVENTION

Figure 1A:
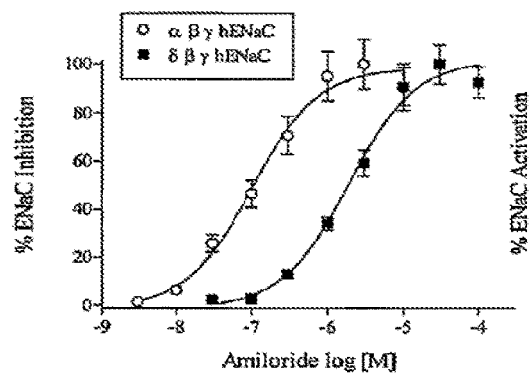
FIGS. 1A and 1B compares human alpha beta gamma and human delta beta gamma ENaC channel function in oocytes in the presence of amiloride.

The subject invention relates to screening assays for identifying human delta epithelial sodium channel (ENaC) enhancers.

As described supra, an inhibitor of ENaC sodium channel function, amiloride, attenuates gustatory responses to sodium chloride in numerous non-mammalian as well as mammalian species, including rodents but not humans. In humans, amiloride has been reported to reduce the intensity of sodium chloride by only 15-20% when used at concentrations that specifically inhibit ENaC function. Experiments performed at Senomyx did not demonstrate a significant effect of amiloride on perceived salt intensity when tested at levels ~300-fold above IC50 values for alpha beta gamma ENaC in oocytes (equivalent to ~10-fold over IC50 values for delta beta gamma ENaC in oocytes). Since delta ENaC is ~25-fold less sensitive to amiloride than alpha ENaC, and human salt taste is poorly inhibited by amiloride, human salt taste may be mediated, in part, by a delta ENaC-based sodium channel. Thus, experiments described infra were used as the basis for the development of novel delta ENaC-based assays to identify delta ENaC enhancers.

Molecular Biology—

α, β, and γ hENaC were cloned from kidney cDNA (Origene, Rockville, Md.) into pcDNA3 (Invitrogen, Carlsbad, Calif.) as described previously (Kellenberger, S and Schild, L. Physiol. Rev. 82:735-767(2002). δ hENaC was cloned from testis cDNA (BD Biosciences Clontech, Palo Alto, Calif.). α hENaC sequence was identical to published sequences from lung and kidney (Rossier et al., Annu. Rev. Physiol. 64:877-897 (2002); Alvarez de la Rosa et al., Annu. Rev. Physiol. 62:573-594 (200). (Genbank accession numbers X76180 and L29007). β hENaC sequence was identical to published sequence from lung Bigiani et al. Bigiani et al., Prog. Biophys. Mol. Biol. 83:193-225 (2003). (Genbank accession number X87159) with the exception of a glycine (nucleotide triplet GGC) to alanine (nucleotide triplet GCC) substitution in our clone at amino acid 314. Inspection of the public single nucleotide polymorphism (SNP) database revealed that glycine 314 and alanine 314 are polymorphisms in β hENaC. γ hENaC sequence was identical to published sequence from placenta (Schild et al., Proc. Natl. Acad. Sci., USA 92:5699-5703 (1995)). (GenBank accession number BC059391). δ hENaC sequence was identical to published sequence from kidney (Shimkets et al., Cell 79: 407414 (1994)) with the exception of a tyrosine (nucleotide triplet TAC) to cysteine (nucleotide triplet TGC) substitution in our clone at amino acid 532. Inspection of the human genome revealed cysteine at amino acid 532, and the public SNP database lists cysteine 532 and tyrosine 532 as polymorphisms in δ hENaC.

In Vitro Transcription—

ENaC cRNA was generated from linearized plasmids using the mMESSAGE mMACHINE kit with T7 RNA polymerase according to the manufacturer's instructions (Ambion, Austin, Tex.). cRNA quality was checked by denaturing agarose gel electrophoresis and spectrophometric absorbance readings at 260 and 280 nm to ensure that full-length, non-degraded cRNA was generated.

Frog Surgery and Oocyte Isolation—

Female *Xenopus laevis* South African clawed frogs greater than or equal to 9 cm in length were obtained from NASCO (Fort Atkinson, Wis.). Frogs were anesthetized in 0.15% ethyl-3-aminobenzoate methanesulfonate (Sigma, St. Louis, Mo.) in distilled water and placed on ice. Using sterile surgical tools, sequential 1-2 cm incisions were made in the abdomen through both the outer skin layer and the inner peritoneal layer to revel the ovaries. Excised ovarian lobes (containing 1000-2000 oocytes) were placed in OR-2 calcium-free media (82.5 mM NaCl, 2 mM KCl, 1 mM $MgCl_2$, 5 mM HEPES pH 7.5 with NaOH) and sequentially digested with 2 mg/ml collagenase type IA (Sigma), prepared immediately before use, for 45 min followed by 1 mg/ml collagenase type IA for 15 min on a rocking platform at room temperature. After enzymatic digestion, at which point the majority of oocytes are released from the ovarian lobes, oocytes were thoroughly rinsed in OR-2 without collagenase and transferred to a Petri dish containing Barth's saline (88 mM NaCl, 2 mM KCl, 0.82 mM $MgSO_4$, 0.33 mM $Ca(NO_3)_2$, 0.41 mM $CaCl_2$, 2.4 mM $NaHCO_3$, and 5 mM HEPES pH 7.5; Specialty Media, Phillipsburg, N.J.) supplemented with 2.5 mM sodium pyruvate. Mature stage V or VI oocytes (~1 mm diameter) were selected for microinjection. Frogs were sutured using a C6 needle with a 3-0 black braid suture (Harvard Apparatus, Holliston, Mass.) and reused for subsequent oocyte isolations following a 2-3 month recovery period.

Microinjection—

Microinjection needles were pulled on a Model P-97 Flaming/Brown Micropipette Puller (Sutter Instrument Co., Novato, Calif.) using borosilicate glass capillaries (World Precision Instruments, Sarasota, Fla.), back-filled with mineral oil (Sigma), and then front-filled with ENaC cRNA using a Nanoliter 2000 injector with a Micro4 MicroSyringe Pump Controller (World Precision Instruments). Oocytes were microinjected in the animal pole with 10-15 nl containing 1 ng of each ENaC subunit cRNA. Following microinjection, oocytes were incubated in Barth's solution supplemented with 2.5 mM sodium pyruvate at 18° C. overnight.

Two Electrode Voltage Clamping—

Unless noted otherwise, ENaC function was measured using the two-electrode voltage clamp technique on an OpusXpress 6000A parallel oocyte voltage clamp system twenty-four hours post-microinjection (Axon Instruments, Union City, Calif.). The OpusXpress system is an integrated workstation that allows electrophysiological recordings to be made from up to 8 oocytes simultaneously. This system has previously been used to examine the function of ion channels including nicotinic acetylcholine and serotonin 5HT3 receptors Snyder et al., Cell 83:969-978 (1995); Grunder et al., Embo J. 16; 899-907 (1997); Chang et al., Nat. Genet. 12:248-253 (1996); Zennaro et al., Trends Endrocrinol. Metab. 15:264-270 (2004); and Bonny et al., Pediatr. Nephrol. 17:804-808 (2002). Oocyte impalement is automated and compound delivery is performed by a computer-controlled fluid handler; compounds are removed from 96-well plates using disposable pipette tips and applied to individual oocytes. Oocytes were placed in the OpusXpress system and perfused with ND-96 solution (96 mM NaCl, 2.5 mM KCl, 1 mM $CaCl_2$, 1 mM $MgCl_2$, and 5 mM HEPES pH 7.5 with NaOH). Oocytes were then impaled with voltage-sensing and current-sensing electrodes back-filled with 3M KCl. Electrodes exhibited resistances between 2-10 Mohm for voltage-sensing electrodes and between 0.5-2 Mohm for current-sensing electrodes. Following impalement, oocytes were voltage clamped to −60 mV and experimental recordings were initiated. Data were acquired at 50 Hz and low-pass filtered at 5 Hz.

Compounds—

The proprietary enhancer compound 6363969 was diluted to appropriate concentrations in ND-96 from 100 mM stock solutions in DMSO. The final concentration of DMSO in experiments was <0.1%; this level of vehicle had no effect on ENaC function in oocytes.

Statistics and Measurements—

Data represent the mean±SEM. Unless otherwise noted, experiments were performed on two to four batches of independently injected oocytes harvested from different frogs. Statistical significance between different groups was determined using an unpaired, two-tailed Student's t-test. Dose-response curves were plotted and both $EC_{50}$ values and Hill coefficients were determined using GraphPad Prism v 3.02 (GraphPad Software, San Diego, Calif.). Values for percent hENaC activation were calculated by dividing the magnitude of the inward current induced by ENaC enhancer compounds by the magnitude of the inward current blocked by amiloride in the same oocyte and multiplying the ratio by 100%.

Results—

Figure 1B:
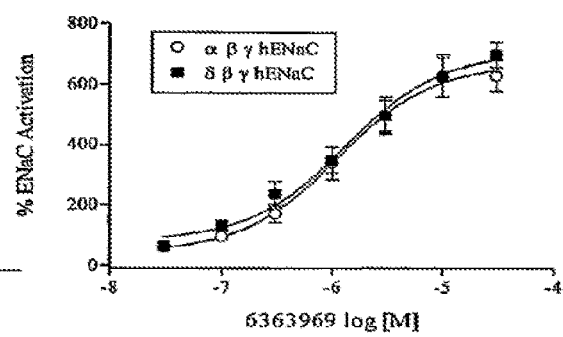
Figure 2A:
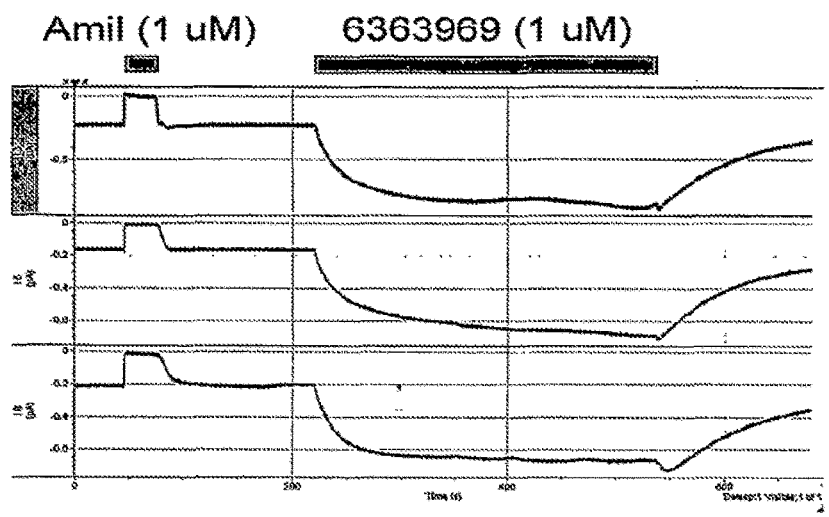
FIGS. 2A and 2B contains representative traces of oocytes expressing wild-type alpha beta gamma hENaC (top traces, FIG. 2A) and delta beta gamma hENaC (bottom traces, FIG. 2B) stimulated with amiloride and a proprietary compound identified by the present Assignee Senomyx Inc. as an ENaC enhancer. Oocytes were stimulated with amiloride (1 uM for alpha ENaC (FIG. 2A) and 10 uM for delta ENaC (FIG. 2B)) and 6363969 (1 uM) (FIGS. 2A and 2B). 6363969 strongly activated both alpha and delta based hENaC channels. Traces show current (uA) on the y-axis as a function of time (sec) on the x-axis.
Figure 2B:
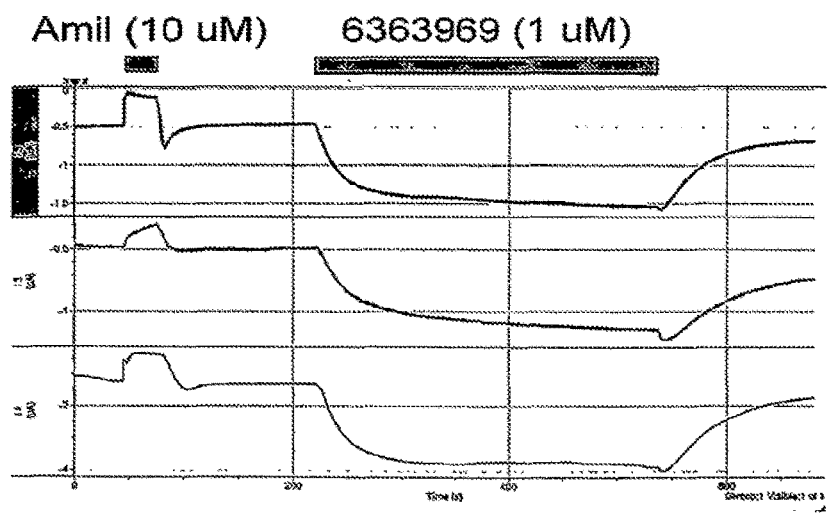

Similar to α hENaC, δ hENaC can form functional amiloride-sensitive channels when expressed alone or in combination with βγ hENaC; however δβγ hENaC is more than an order of magnitude less sensitive to amiloride compared to αβγ hENaC Shimkets et al., Cell 79:407-414 (1994); and Bonny et al., J. Clin. Invest. 104:967-974 (1999). α hENaC (human ENaC) and δ hENaC are 58% identical at the DNA level and 35% identical at the protein level. Expression of δβγ hENaC generated amiloride-sensitive currents; the $IC_{50}$ for amiloride inhibition of δβγ hENaC was 2.7±0.3 uM (n=10), similar to previous reports Shimkets et al., (Id.); Bonny et al. (Id.), and much larger than the $IC_{50}$ for amiloride inhibition of αβγ hENaC (110±11 nM; n=16) (FIG. 1A). Activation of δβγ hENaC by 6363969 was similar to αβγ hENaC (FIG. 1B); the $EC_{50}$ for 6363969 activation of δβγ hENaC was 1.2±0.2 uM (n=11) compared to the $EC_{50}$ for 6363969 activation of αβγhENaC of 1.2±0.1 uM (n=46). Representative traces illustrating the effect of 6363969 on alpha and delta ENaC are shown in FIGS. 2A and 2B. Compounds from different chemical classes were tested on alpha and delta-based hENaC channels; all chemical classes activated alpha and delta ENaC with similar efficacy and potency (Table 1).

Based on the foregoing, the present invention uses cell-based assays to identify delta human ENaC modulators (enhancers). These compounds have potential application in modulating human salty taste perception. Compounds identified in the subject electrophysiological assays and their biologically acceptable derivatives are to be tested in human taste tests using human volunteers to confirm their effect on human salty taste perception.

As discussed further infra, these cell-based assays preferably use high throughput screening platforms to identify compounds that modulate (enhance) ENaC activity using cells that express human delta beta gamma ENaCs. The sequences of these respective human delta, beta and gamma subunits are provided infra. Additionally, these sequences may be modified to introduce silent mutations or mutations having a functional effect such as defined mutations that affect sodium ion influx. As noted above, the assays will preferably comprise electrophysiological assays effected in amphibian oocytes or assays using mammalian cells that express a human delta beta gamma ENaC using fluorescent ion sensitive dyes or membrane potential dyes, e.g., sodium-sensitive dyes. Preferably, compounds that modulate ENaC are identified by screening using electrophysiological assays effected with oocytes that express a human delta beta gamma ENaC (e.g., patch clamping or two electrode voltage clamping).

Still alternatively, compounds that modulate ENaC may be detected by ion flux assays, e.g., radiolabeled-ion flux assays or atomic absorption spectroscopic coupled ion flux assays. As disclosed supra, these ENaC enhancers have potential application in modulating human salty taste perception or for modulating other biological processes involving aberrant or normal ENaC function.

The subject cell-based assays use mutant ENaC nucleic acid sequences which are expressed in desired cells, preferably oocytes or human cells such as human kidney two hundred and nintey-three cells, or other human or mammalian cells conventionally used in screens for identifying ion channel modulatory compounds. These cells may further be engineered to express other sequences, e.g., taste GPCRs, i.e., T1Rs or T2Rs such as are described in other patent applications by the present Assignee Senomyx. The oocyte system is advantageous as it allows for direct injection of multiple mRNA species, provides for high protein expression and can accommodate the deleterious effects inherent in the overexpression of ENaC. The drawbacks are however that electrophysiological screening using amphibian oocytes is not as amenable to high throughput screening of large numbers of compounds and is not a mammalian system. As noted, the present invention embraces human delta beta gamma ENaC assays using mammalian cells, preferably high throughput assays.

ENaC proteins are known to form heteromeric channels comprised of three subunits, an alpha, beta, and a gamma or delta subunit. The sequences of these respective ENaC subunits are disclosed in an earlier published patent application by the present Assignee, U.S. Ser. No. 10/133,573 which is incorporated by reference in its entirety herein.

Additionally, the sequences for these respective subunits are contained in the Sequence Listing that immediately precedes the claims of the subject application. Upon co-expression in a suitable cell these subunits result in a heterotrimeric channel having ion channel cation channel activity; in particular it responds to sodium and should similarly respond to lithium ions in cell-based assays such as those which are disclosed herein and in Senomyx's prior patent application referenced above.

Also different splice variants of these ENaC subunit sequences are known with some being the subject of recently filed provisional applications by the present Assignee. See also U.S. Pat. No. 5,693,756 incorporated by reference in its entirety herein.

The ENaC channel has relatively high permeability to sodium and lithium and is amiloride-sensitive. Channel activity can be effectively measured, e.g., by recording ligand-induced changes in [Na$^+$] and measuring sodium or lithium ion influx using fluorescent ion-indicator dyes and fluorimetric imaging. ENaC is expressed in a number of epithelial tissues, including taste buds. Additionally, ENaC function is involved in kidney, lung function, blood pressure regulation et al. as disclosed above. Consequently, compounds identified as ENaC modulators have significant potential human therapeutic applications.

The Senomyx application incorporated by reference provides high throughput screening assays using mammalian cells transfected or seeded into wells or culture plates wherein functional expression in the presence of test compounds is allowed to proceed and activity is detected using membrane-potential fluorescent or ion (sodium) fluorescent dyes.

As discussed above, the invention specifically provides methods of screening for modulators, e.g., activators, inhibitors, stimulators, enhancers, etc., of human delta ENaC nucleic acids and proteins, using the human ENaC nucleic acid sequences provided herein. Such modulators can affect ENaC activity, e.g., by modulating ENaC transcription, translation, mRNA or protein stability; by altering the interaction of ENaC with the plasma membrane, or other molecules; or by affecting ENaC protein activity. Compounds are screened, e.g., using high throughput screening (HTS), to identify those compounds that can bind to and/or modulate the activity of a ENaC polypeptide or fragment thereof. In the present invention, ENaC proteins are recombinantly expressed in cells, e.g., human cells, or frog oocytes and the modulation of ENaC is assayed by using any measure of ion channel function, such as measurement of the membrane potential, or measures of changes in intracellular sodium or lithium levels. Methods of assaying ion, e.g., cation, channel function include, for example, patch clamp techniques, two electrode voltage clamping, measurement of whole cell currents, and fluorescent imaging techniques that use ion-sensitive fluorescent dyes and ion flux assays, e.g., radiolabeled-ion flux assays or ion flux assays.

A human delta ENaC agonist identified as set forth in the current application can be used for a number of different purposes. For example, a ENaC activator can be included as a flavoring agent to modulate the salty taste of foods, beverages, soups, medicines, and other products for human consumption. Additionally, the invention provides kits for carrying out the herein-disclosed assays.

DEFINITIONS

An ENaC associated biological function condition preferably refers to human salty taste perception.

"Cation channels" are a diverse group of proteins that regulate the flow of cations across cellular membranes. The ability of a specific cation channel to transport particular cations typically varies with the valency of the cations, as well as the specificity of the given channel for a particular cation.

"Homomeric channel" refers to a cation channel composed of identical alpha subunits, whereas "heteromeric channel" refers to a cation channel composed of two or more different types of alpha subunits. Both homomeric and heteromeric channels can include auxiliary beta subunits.

A "beta subunit" or "gamma subunit" is a polypeptide monomer that is an auxiliary subunit of a cation channel composed of alpha subunits; however, beta or gamma subunits alone cannot form a channel (see, e.g., U.S. Pat. No. 5,776,734). Beta or gamma subunits are known, for example, to increase the number of channels by helping the alpha or delta subunits reach the cell surface, change activation kinetics, and change the sensitivity of natural ligands binding to the channels. Beta or gamma subunits can be outside of the pore region and associated with alpha or delta subunits comprising the pore region. They can also contribute to the external mouth of the pore region.

The term "authentic" or "wild-type" or "native" human ENaC nucleic acid sequences refer to the wild-type and mutant alpha, beta, gamma and delta nucleic acid sequences contained in the Sequence Listing that immediately precedes the claims as well as splice variants and other ENaC nucleic acid sequences generally known in the art.

The term "authentic" or "wild-type" or "native" human ENaC polypeptides refers to the polypeptides encoded by the nucleic acid sequence contained in SEQ ID NO: 1, 3 and 5 and contained in SEQ ID NO:2, 4 and 6.

The term "modified hENaC nuclear acid sequence" or "optimized hENaC nucleic acid sequence" refers to a hENaC nucleic acid sequence which contains one or mutation that, particularly those that affect (inhibit or prevent) ENaC activity in recombinant host cells, and most especially oocytes or human cells such as human kidney two hundred and ninety-three cells. Particularly, these mutations include those that affect gating by the resultant ENaC channel containing the mutated subunit sequence. The ENaC may comprise such mutations in one or several of the three subunits that constitute the ENaC. The modified ENaC nucleic acid sequence contains substitution mutations in one subunit that affect (impair) gating function or defective surface expression. The invention embraces the use of other mutated ENaC sequences, i.e., delta subunit mutants, e.g., splice variants, those containing deletions or additions, chimeras of the subject ENaC sequences and the like. Further, the invention may use ENaC subunit sequences which may be modified to introduce host cell preferred codons, particularly amphibian or human host cell preferred codons.

The term "ENaC" protein or fragment thereof, or a nucleic acid encoding "ENaC" or a fragment thereof refer to nucleic acids and polypeptide polymorphic variants, alleles, mutants, and interspecies homologs that: (1) have an amino acid sequence that has greater than about 60% amino acid sequence identity, 65%, 70%, 75%, 80%, 85%, 90%, preferably 91%, 92%, 93%, 94%, 95%, 96%, 97%, 98% or 99% or greater amino acid sequence identity, preferably over a region of at least about 25, 50, 100, 200, 500, 1000, or more amino acids, to an amino acid sequence encoded by a ENaC nucleic acid or amino acid sequence of a ENaC protein, e.g., the ENaC subunit proteins encoded by the ENaC nucleic acid sequences contained in the Sequence Listing that precedes the claims of this application as well as fragments thereof, and conservatively modified variants thereof; (3) polypeptides encoded by nucleic acid sequences which specifically hybridize under stringent hybridization conditions to an anti-sense strand corresponding to a nucleic acid sequence encoding a ENaC protein subunit, and conservatively modified variants thereof; (4) have a nucleic acid sequence that has greater than about 60% sequence identity, 65%, 70%, 75%, 80%, 85%, 90%, preferably 91%, 92%, 93%, 94%, 95%, 96%, 97%, 98% or 99%, or higher nucleotide sequence identity, preferably over a region of at least about 25, 50, 100, 200, 500, 1000, or more nucleotides, to a ENaC nucleic acid, e.g., those disclosed herein.

An ENaC polynucleotide or polypeptide sequence is typically from a mammal including, but not limited to, primate, e.g., human; rodent, e.g., rat, mouse, hamster; cow, pig, horse, sheep, or any mammal. The nucleic acids and proteins of the invention include both naturally occurring or recombinant molecules. ENaC proteins typically have ion channel activity, i.e., they are permeable to sodium or lithium.

By "determining the functional effect" or "determining the effect on the cell" is meant assaying the effect of a compound that increases or decreases a parameter that is indirectly or directly under the influence of a ENaC polypeptide e.g., functional, physical, phenotypic, and chemical effects. Such functional effects include, but are not limited to, changes in ion flux, membrane potential, current amplitude, and voltage gating, as well as other biological effects such as changes in gene expression of ENaC or of any marker genes, and the like. The ion flux can include any ion that passes through the channel, e.g., sodium or lithium, and analogs thereof such as radioisotopes. Such functional effects can be measured by any means known to those skilled in the art, e.g., patch clamping, using voltage-sensitive dyes, or by measuring changes in parameters such as spectroscopic characteristics (e.g., fluorescence, absorbance, refractive index), hydrodynamic (e.g., shape), chromatographic, or solubility properties.

"Inhibitors," "activators," and "modulators" of ENaC polynucleotide and polypeptide sequences are used to refer to activating, inhibitory, or modulating molecules identified using in vitro and in vivo assays of ENaC polynucleotide and polypeptide sequences. Inhibitors are compounds that, e.g., bind to, partially or totally block activity, decrease, prevent, delay activation, inactivate, desensitize, or down regulate the activity or expression of ENaC proteins, e.g., antagonists.

"Activators" are compounds that increase, open, activate, facilitate, enhance activation, sensitize, agonize, or up regulate ENaC protein activity. Inhibitors, activators, or modulators also include genetically modified versions of ENaC proteins, e.g., versions with altered activity, as well as naturally occurring and synthetic ligands, antagonists, agonists, peptides, cyclic peptides, nucleic acids, antibodies, antisense molecules, siRNA, ribozymes, small organic molecules and the like. Such assays for inhibitors and activators include, e.g., expressing ENaC protein in vitro, in cells, cell extracts, or cell membranes, applying putative modulator compounds, and then determining the functional effects on activity, as described above.

Samples or assays comprising ENaC proteins that are treated with a potential activator, inhibitor, or modulator are compared to control samples without the inhibitor, activator, or modulator to examine the extent of activation or migration modulation. Control samples (untreated with inhibitors) are assigned a relative protein activity value of 100%. Inhibition of ENaC is achieved when the activity value relative to the control is about 80%, preferably 50%, more preferably 25-0%. Activation of ENaC is achieved when the activity value relative to the control (untreated with activators) is 110%, more preferably 150%, more preferably 200-500% (i.e., two to five fold higher relative to the control), more preferably 1000-3000% higher.

The term "test compound" or "drug candidate" or "modulator" or grammatical equivalents as used herein describes any molecule, either naturally occurring or synthetic compound, preferably a small molecule, or a protein, oligopeptide (e.g., from about 5 to about 25 amino acids in length, preferably from about 10 to 20 or 12 to 18 amino acids in length, preferably 12, 15, or 18 amino acids in length), small organic molecule, polysaccharide, lipid, fatty acid, polynucleotide, siRNA, oligonucleotide, ribozyme, etc., to be tested for the capacity to modulate ENaC function. The test compound can be in the form of a library of test compounds, such as a combinatorial or randomized library that provides a sufficient range of diversity. Test compounds are optionally linked to a fusion partner, e.g., targeting compounds, rescue compounds, dimerization compounds, stabilizing compounds, addressable compounds, and other functional moieties. Conventionally, new chemical entities with useful properties are generated by identifying a test compound (called a "lead compound") with some desirable property or activity, e.g., inhibiting activity, creating variants of the lead compound, and evaluating the property and activity of those variant compounds. Often, high throughput screening (HTS) methods are employed for such an analysis.

A "small organic molecule" refers to an organic molecule, either naturally occurring or synthetic, that has a molecular weight of more than about 50 daltons and less than about 2500 daltons, preferably less than about 2000 daltons, preferably between about 100 to about 1000 daltons, more preferably between about 200 to about 500 daltons.

"Biological sample" include sections of tissues such as biopsy and autopsy samples, and frozen sections taken for histologic purposes. Such samples include blood, sputum, tissue, cultured cells, e.g., primary cultures, explants, and transformed cells, stool, urine, etc. A biological sample is typically obtained from a eukaryotic organism, most preferably a mammal such as a primate e.g., chimpanzee or human; cow; dog; cat; a rodent, e.g., guinea pig, rat, mouse; rabbit; or a bird; reptile; or fish.

The terms "identical" or percent "identity," in the context of two or more nucleic acids or polypeptide sequences, refer to two or more sequences or subsequences that are the same or have a specified percentage of amino acid residues or nucleotides that are the same (i.e., about 60% identity, preferably 65%, 70%, 75%, 80%, 85%, 90%, 91%, 92%, 93%, 94%, 95%, 96%, 97%, 98%, 99%, or higher identity over a specified region (e.g., ENaC nucleotide sequences contained in the Sequence Listing), when compared and aligned for maximum correspondence over a comparison window or designated region) as measured using a BLAST or BLAST 2.0 sequence comparison algorithms with default parameters described below, or by manual alignment and visual inspection (see, e.g., NCBI web site or the like). Such sequences are then said to be "substantially identical." This definition also refers to, or may be applied to, the compliment of a test sequence. The definition also includes sequences that have deletions and/or additions, as well as those that have substitutions. As described below, the preferred algorithms can account for gaps and the like. Preferably, identity exists over a region that is at least about 25 amino acids or nucleotides in length, or more preferably over a region that is 50-100 amino acids or nucleotides in length.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Preferably, default program parameters can be used, or alternative parameters can be designated. The sequence comparison algorithm then calculates the percent sequence identities for the test sequences relative to the reference sequence, based on the program parameters.

A "comparison window", as used herein, includes reference to a segment of any one of the number of contiguous positions selected from the group consisting of from 20 to 600, usually about 50 to about 200, more usually about 100 to about 150 in which a sequence may be compared to a reference sequence of the same number of contiguous positions after the two sequences are optimally aligned. Methods of alignment of sequences for comparison are well-known in the art. Optimal alignment of sequences for comparison can be conducted, e.g., by the local homology algorithm of Smith & Waterman, Adv. Appl. Math. 2:482 (1981), by the homology alignment algorithm of Needleman & Wunsch, J. Mol. Biol. 48:443 (1970), by the search for similarity method of Pearson & Lipman, Proc. Nat'l. Acad. Sci. USA 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., Current Protocols in Molecular Biology (Ausubel et al., eds. 1995 supplement)).

A preferred example of algorithm that is suitable for determining percent sequence identity and sequence similarity are the BLAST and BLAST 2.0 algorithms, which are described in Altschul et al., Nucl. Acids Res. 25:3389-3402 (1977) and Altschul et al., J. Mol. Biol. 215:403410 (1990), respectively. BLAST and BLAST 2.0 are used, with the parameters described herein, to determine percent sequence identity for the nucleic acids and proteins of the invention. Software for performing BLAST analyses is publicly available through the National Center for Biotechnology Information. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a word length (W) of 11, an expectation (E) of 10, M=5, N=−4 and a comparison of both strands. For amino acid sequences, the BLASTP program uses as defaults a word length of 3, and expectation (E) of 10, and the BLOSUM62 scoring matrix (see Henikoff & Henikoff, Proc. Natl. Acad. Sci., USA 89:10915 (1989)) alignments (B) of 50, expectation (E) of 10, M=5, N=−4, and a comparison of both strands.

"Nucleic acid" refers to deoxyribonucleotides or ribonucleotides and polymers thereof in either single- or double-stranded form, and complements thereof. The term encompasses nucleic acids containing known nucleotide analogs or modified backbone residues or linkages, which are synthetic, naturally occurring, and non-naturally occurring, which have similar binding properties as the reference nucleic acid and which are metabolized in a manner similar to the reference nucleotides. Examples of such analogs include, without limitation, phosphorothioates, phosphoramidates, methyl phosphonates, chiral-methyl phosphonates, 2-O-methyl ribonucleotides, peptide-nucleic acids (PNAs).

Unless otherwise indicated, a particular nucleic acid sequence also implicitly encompasses conservatively modified variants thereof (e.g., degenerate codor substitutions) and complementary sequences, as well as the sequence explicitly indicated. Specifically, degenerate codon substitutions may be achieved by generating sequences in which the third position of one or more selected (or all) codons is substituted with mixed-base and/or deoxyinosine residues (Batzer et al., Nucleic Acid Res. 19:5081 (1991); Ohtsuka et al., J. Biol. Chem. 260:2605-2608 (1985); Rossolini et al., Mol. Cell. Probes 8:91-98 (1994)). The term nucleic acid is used interchangeably with gene, cDNA, mRNA, oligonucleotide, and polynucleotide.

A particular nucleic acid sequence also implicitly encompasses "splice variants." Similarly, a particular protein encoded by a nucleic acid implicitly encompasses any protein encoded by a splice variant of that nucleic acid. "Splice variants," as the name suggests, are products of alternative splicing of a gene. After transcription, an initial nucleic acid transcript may be spliced such that different (alternate) nucleic acid splice products encode different polypeptides. Mechanisms for the production of splice variants vary, but include alternate splicing of exons. Alternate polypeptides derived from the same nucleic acid by read-through transcription are also encompassed by this definition. Any products of a splicing reaction, including recombinant forms of the splice products, are included in this definition. An example of potassium channel splice variants is discussed in Leicher, et al., J. Biol. Chem. 273(52):35095-35101 (1998).

The terms "polypeptide," "peptide" and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymer.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally occurring amino acid, i.e., an a carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions in a manner similar to a naturally occurring amino acid.

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

"Conservatively modified variants" applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid which encodes a polypeptide is implicit in each described sequence with respect to the expression product, but not with respect to actual probe sequences.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the invention.

The following eight groups each contain amino acids that are conservative substitutions for one another: 1) Alanine (A), Glycine (G); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); 6) Phenylalanine (F), Tyrosine (Y), Tryptophan (W); 7) Serine (S), Threonine (T); and 8) Cysteine (C), Methionine (M) (see, e.g., Creighton, Proteins (1984)).

Macromolecular structures such as polypeptide structures can be described in terms of various levels of organization. For a general discussion of this organization, see, e.g., Alberts et al., Molecular Biology of the Cell (3rd ed., 1994) and Cantor and Schimmel, Biophysical Chemistry Part I: The Conformation of Biological Macromolecules (1980).

"Primary structure" refers to the amino acid sequence of a particular peptide. "Secondary structure" refers to locally ordered, three dimensional structures within a polypeptide. These structures are commonly known as domains, e.g., transmembrane domains, pore domains, and cytoplasmic tail domains. Domains are portions of a polypeptide that form a compact unit of the polypeptide and are typically 15 to 350 amino acids long. Exemplary domains include extracellular domains, transmembrane domains, and cytoplasmic domains. Typical domains are made up of sections of lesser organization such as stretches of .beta.-sheet and .alpha.-helices. "Tertiary structure" refers to the complete three dimensional structure of a polypeptide monomer. "Quaternary structure" refers to the three dimensional structure formed by the noncovalent association of independent tertiary units. Anisotropic terms are also known as energy terms.

A "label" or a "detectable moiety" is a composition detectable by spectroscopic, photochemical, biochemical, immunochemical, chemical, or other physical means. For example, useful labels include 32P, fluorescent dyes, electron-dense reagents, enzymes (e.g., as commonly used in an ELISA), biotin, digoxigenin, or haptens and proteins which can be made detectable, e.g., by incorporating a radiolabel into the peptide or used to detect antibodies specifically reactive with the peptide.

The term "recombinant" when used with reference, e.g., to a cell, or nucleic acid, protein, or vector, indicates that the cell, nucleic acid, protein or vector, has been modified by the introduction of a heterologous nucleic acid or protein or the alteration of a native nucleic acid or protein, or that the cell is derived from a cell so modified. Thus, for example, recombinant cells express genes that are not found within the native (non-recombinant) form of the cell or express native genes that are otherwise abnormally expressed, under expressed or not expressed at all.

The term "heterologous" when used with reference to portions of a nucleic acid indicates that the nucleic acid comprises two or more subsequences that are not found in the same relationship to each other in nature. For instance, the nucleic acid is typically recombinantly produced, having two or more sequences from unrelated genes arranged to make a new functional nucleic acid, e.g., a promoter from one source and a coding region from another source. Similarly, a heterologous protein indicates that the protein comprises two or more subsequences that are not found in the same relationship to each other in nature (e.g., a fusion protein).

The phrase "stringent hybridization conditions" refers to conditions under which a probe will hybridize to its target subsequence, typically in a complex mixture of nucleic acids, but to no other sequences. Stringent conditions are sequence-dependent and will be different in different circumstances. Longer sequences hybridize specifically at higher temperatures. An extensive guide to the hybridization of nucleic acids is found in Tijssen, Techniques in Biochemistry and Molecular Biology—Hybridization with Nucleic Probes, "Overview of principles of hybridization and the strategy of nucleic acid assays" (1993). Generally, stringent conditions are selected to be about 5-10° C. lower than the thermal melting point ($T_m$) for the specific sequence at a defined ionic strength pH. The $T_m$ is the temperature (under defined ionic strength, pH and nucleic concentration) at which 50% of the probes complementary to the target hybridize to the target sequence at equilibrium (as the target sequences are present in excess, at $T_m$, 50% of the probes are occupied at equilibrium). Stringent conditions may also be achieved with the addition of destabilizing agents such as formamide. For selective or specific hybridization, a positive signal is at least two times background, preferably 10 times background hybridization. Exemplary stringent hybridization conditions can be as following: 50% formamide, 5×SSC, and 1% SDS, incubating at 42° C., or, 5×SSC, 1% SDS, incubating at 65° C., with wash in 0.2.times. SSC, and 0.1% SDS at 65° C.

Nucleic acids that do not hybridize to each other under stringent conditions are still substantially identical if the polypeptides which they encode are substantially identical. This occurs, for example, when a copy of a nucleic acid is created using the maximum codon degeneracy permitted by the genetic code. In such cases, the nucleic acids typically hybridize under moderately stringent hybridization conditions. Exemplary "moderately stringent hybridization conditions" include a hybridization in a buffer of 40% formamide, 1 M NaCl, 1% SDS at 37° C., and a wash in 1.times. SSC at 45° C. A positive hybridization is at least twice background. Those of ordinary skill will readily recognize that alternative hybridization and wash conditions can be utilized to provide conditions of similar stringency. Additional guidelines for determining hybridization parameters are provided in numerous reference, e.g., and Current Protocols in Molecular Biology, ed. Ausubel, et al.

For PCR, a temperature of about 36° C. is typical for low stringency amplification, although annealing temperatures may vary between about 32° C. and 48° C. depending on primer length. For high stringency PCR amplification, a temperature of about 62° C. is typical, although high stringency annealing temperatures can range from about 50° C. to about 65° C., depending on the primer length and specificity. Typical cycle conditions for both high and low stringency amplifications include a denaturation phase of 90° C.-95° C. for 30 sec-2 min., an annealing phase lasting 30 sec.-2 min., and an extension phase of about 72° C. for 1-2 min. Protocols and guidelines for low and high stringency amplification reactions are provided, e.g., in Innis et al. (1990) PCR Protocols, A Guide to Methods and Applications, Academic Press, Inc. N.Y.).

"Antibody" refers to a polypeptide comprising a framework region from an immunoglobulin gene or fragments thereof that specifically binds and recognizes an antigen. The recognized immunoglobulin genes include the kappa, lambda, alpha, gamma, delta, epsilon, and mu constant region genes, as well as the myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively. Typically, the antigen-binding region of an antibody will be most critical in specificity and affinity of binding.

The term antibody, as used herein, also includes antibody fragments either produced by the modification of whole antibodies, or those synthesized de novo using recombinant DNA methodologies (e.g., single chain Fv), chimeric, humanized or those identified using phage display libraries (see, e.g., McCafferty et al., Nature 348:552-554 (1990)) For preparation of antibodies, e.g., recombinant, monoclonal, or polyclonal antibodies, many technique known in the art can be used (see, e.g., Kohler & Milstein, Nature 256:495497 (1975); Kozbor et al., Immunology Today 4: 72 (1983); Cole et al., pp. 77-96 in Monoclonal Antibodies and Cancer Therapy, Alan R. Liss, Inc. (1985); Coligan, Current Protocols in Immunology (1991); Harlow & Lane, Antibodies, A Laboratory Manual (1988) and Harlow & Lane, Using Antibodies, A Laboratory Manual (1999); and Goding, Monoclonal Antibodies: Principles and Practice (2d ed. 1986)).

The phrase "specifically (or selectively) binds" to an antibody or "specifically (or selectively) immunoreactive with," when referring to a protein or peptide, refers to a binding reaction that is determinative of the presence of the protein, often in a heterogeneous population of proteins and other biologics. Thus, under designated immunoassay conditions, the specified antibodies bind to a particular protein at least two times the background and more typically more than 10 to 100 times background. Specific binding to an antibody under such conditions requires an antibody that is selected for its specificity for a particular protein. For example, polyclonal antibodies raised to ENaC protein, polymorphic variants, alleles, orthologs, and conservatively modified variants, or splice variants, or portions thereof, can be selected to obtain only those polyclonal antibodies that are specifically immunoreactive with ENaC proteins and not with other proteins. This selection may be achieved by subtracting out antibodies that cross-react with other molecules. A variety of immunoassay formats may be used to select antibodies specifically immunoreactive with a particular protein. For example, solid-phase ELISA immunoassays are routinely used to select antibodies specifically immunoreactive with a protein (see, e.g., Harlow & Lane, Antibodies, A Laboratory Manual (1988) for a description of immunoassay formats and conditions that can be used to determine specific immunoreactivity).

By "therapeutically effective dose" herein is meant a dose that produces effects for which it is administered. The exact dose will depend on the purpose of the treatment, and will be ascertainable by one skilled in the art using known techniques (see, e.g., Lieberman, Pharmaceutical Dosage Forms (vols. 1-3, 1992); Lloyd, The Art, Science and Technology of Pharmaceutical Compounding (1999); and Pickar, Dosage Calculations (1999)).

Recombinant Expression of ENaC

To obtain high level expression of a cloned gene, such as those cDNAs encoding ENaC, one typically subclones ENaC into an expression vector that contains a strong promoter to direct transcription, a transcription/translation terminator, and if for a nucleic acid encoding a protein, a ribosome binding site for translational initiation. Suitable eukaryotic and prokaryotic promoters are well known in the art and described, e.g., in Sambrook et al., and Ausubel et al., supra. For example, bacterial expression systems for expressing the ENaC protein are available in, e.g., *E. coli, Bacillus* sp., and *Salmonella* (Palva et al., Gene 22:229-235 (1983); Mosbach et al., Nature 302:543-545 (1983). Kits for such expression systems are commercially available. Eukaryotic expression systems for mammalian cells, yeast, and insect cells are well known in the art and are also commercially available. For example, retroviral expression systems may be used in the present invention. As described infra, the subject modified hENaC is preferably expressed in human cells such as human kidney two hundred and ninety-three cells which are widely used for high throughput screening.

Selection of the promoter used to direct expression of a heterologous nucleic acid depends on the particular application. The promoter is preferably positioned about the same distance from the heterologous transcription start site as it is from the transcription start site in its natural setting. As is known in the art, however, some variation in this distance can be accommodated without loss of promoter function.

In addition to the promoter, the expression vector typically contains a transcription unit or expression cassette that contains all the additional elements required for the expression of the ENaC-encoding nucleic acid in host cells. A typical expression cassette thus contains a promoter operably linked to the nucleic acid sequence encoding ENaC and signals required for efficient polyadenylation of the transcript, ribosome binding sites, and translation termination. Additional elements of the cassette may include enhancers and, if genomic DNA is used as the structural gene, introns with functional splice donor and acceptor sites. As noted previously, the exemplified modified hENaC is modified to remove putative cryptic splice donor and acceptor sites.

In addition to a promoter sequence, the expression cassette should also contain a transcription termination region downstream of the structural gene to provide for efficient termination. The termination region may be obtained from the same gene as the promoter sequence or may be obtained from different genes.

The particular expression vector used to transport the genetic information into the cell is not particularly critical. Any of the conventional vectors used for expression in eukaryotic or prokaryotic cells may be used. Standard bacterial expression vectors include plasmids such as pBR322 based plasmids, pSKF, pET23D, and fusion expression systems such as MBP, GST, and LacZ. Epitope tags can also be added to recombinant proteins to provide convenient methods of isolation, e.g., c-myc. Sequence tags may be included in an expression cassette for nucleic acid rescue. Markers such as fluorescent proteins, green or red fluorescent protein, β-gal, CAT, and the like can be included in the vectors as markers for vector transduction.

Expression vectors containing regulatory elements from eukaryotic viruses are typically used in eukaryotic expression vectors, e.g., SV40 vectors, papilloma virus vectors, retroviral vectors, and vectors derived from Epstein-Barr virus. Other exemplary eukaryotic vectors include pMSG, pAV009/A+, pMTO10/A+, pMAMneo-5, baculovirus pDSVE, and any other vector allowing expression of proteins under the direction of the CMV promoter, SV40 early promoter, SV40 later promoter, metallothionein promoter, murine mammary tumor virus promoter, Rous sarcoma virus promoter, polyhedrin promoter, or other promoters shown effective for expression in eukaryotic cells.

Expression of proteins from eukaryotic vectors can be also be regulated using inducible promoters. With inducible promoters, expression levels are tied to the concentration of inducing agents, such as tetracycline or ecdysone, by the incorporation of response elements for these agents into the promoter. Generally, high level expression is obtained from inducible promoters only in the presence of the inducing agent; basal expression levels are minimal.

The vectors used in the invention may include a regulatable promoter, e.g., tet-regulated systems and the RU-486 system (see, e.g., Gossen & Bujard, Proc. Nat'l Acad. Sci USA 89:5547 (1992); Oligino et al., Gene Ther. 5:491-496 (1998); Wang et al., Gene Ther. 4:432-441 (1997); Neering et al., Blood 88:1147-1155 (1996); and Rendahl et al., Nat. Biotechnol. 16:757-761 (1998)). These impart small molecule control on the expression of the candidate target nucleic acids. This beneficial feature can be used to determine that a desired phenotype is caused by a transfected cDNA rather than a somatic mutation.

Some expression systems have markers that provide gene amplification such as thymidine kinase and dihydrofolate reductase. Alternatively, high yield expression systems not involving gene amplification are also suitable, such as using a baculovirus vector in insect cells, with a ENaC encoding sequence under the direction of the polyhedrin promoter or other strong baculovirus promoters.

The elements that are typically included in expression vectors also include a replicon that functions in the particular host cell. In the case of E. coli, the vector may contain a gene encoding antibiotic resistance to permit selection of bacteria that harbor recombinant plasmids, and unique restriction sites in nonessential regions of the plasmid to allow insertion of eukaryotic sequences. The particular antibiotic resistance gene chosen is not critical, any of the many resistance genes known in the art are suitable. The prokaryotic sequences are preferably chosen such that they do not interfere with the replication of the DNA in eukaryotic cells, if necessary.

Standard transfection methods may be used to produce bacterial, mammalian, yeast or insect cell lines that express large quantities of ENaC protein, which are then purified using standard techniques (see, e.g., Colley et al., J. Biol. Chem. 264:17619-17622 (1989); Guide to Protein Purification, in Methods in Enzymology, Vol. 182 (Deutscher, ed., 1990)). Transformation of eukaryotic and prokaryotic cells are performed according to standard techniques (see, e.g., Morrison, J. Bact. 132:349-351 (1977); Clark-Curtiss & Curtiss, Methods in Enzymology 101:347-362 (Wu et al., eds, 1983). Any of the well-known procedures for introducing foreign nucleotide sequences into host cells may be used. These include the use of calcium phosphate transfection, polybrene, protoplast fusion, electroporation, biolistics, liposomes, microinjection, plasma vectors, viral vectors and any of the other well known methods for introducing cloned genomic DNA, cDNA, synthetic DNA or other foreign genetic material into a host cell (see, e.g., Sambrook et al., supra). It is only necessary that the particular genetic engineering procedure used be capable of successfully introducing at least one gene into the host cell capable of expressing ENaC.

After the expression vector is introduced into the cells, the transfected cells are cultured under conditions favoring expression of ENaC. In some instances, such ENaC polypeptides may be recovered from the culture using standard techniques identified below.

Assays for Modulators of Delta ENaC Protein

Modulation of an ENaC protein, can be assessed using a variety of in vitro and in vivo assays, including cell-based models as described above. Such assays can be used to test for inhibitors and activators of ENaC protein or fragments thereof, and, consequently, inhibitors and activators of ENaC. Such modulators of ENaC protein are useful as flavorings to modulate ENaC associated salty taste.

As noted above, the ENaC protein used in the subject cell based assays will preferably be encoded by hENaC nucleic acid sequences encoding subunits that comprise at least one mutation which affects (reduces) ENaC function relative to the corresponding wild-type ENaC as the assays preferably screen for compounds (enhancers) capable of "restoring" the function thereof in specific cells, preferably frog oocytes or mammalian cells, preferably human cells. These sequences include those exemplified in the examples infra.

Compounds identified in such assays will then be evaluated in vivo to confirm that this affect on ENaC is obtained in vivo and consequently that the identified compound is suitable for correcting or modulating a function involving ENaC such as those afore-identified. Assays using cells expressing ENaC proteins, either recombinant or naturally occurring, can be performed using a variety of assays, in vitro, in vivo, and ex vivo, as described herein. To identify molecules capable of modulating ENaC, assays are performed to detect the effect of various candidate modulators on ENaC activity preferably a mutant ENaC in a cell.

The channel activity of ENaC proteins can be assayed using a variety of assays to measure changes in ion fluxes including patch clamp techniques, measurement of whole cell currents, radiolabeled ion flux assays or a flux assay coupled to atomic absorption spectroscopy, and fluorescence assays using voltage-sensitive dyes or lithium or sodium sensitive dyes (see, e.g., Vestergarrd-Bogind et al., J. Membrane Biol. 88:67-75 (1988); Daniel et al., J. Pharmacol. Meth. 25:185-193 (1991); Hoevinsky et al., J. Membrane Biol. 137:59-70 (1994)). For example, a nucleic acid encoding an ENaC protein or homolog thereof can be injected into *Xenopus oocytes* or transfected into mammalian cells, preferably human cells such as human kidney two hundred and ninety-three cells. Channel activity can then be assessed by measuring changes in membrane polarization, i.e., changes in membrane potential.

A preferred means to obtain electrophysiological measurements is by measuring currents using patch clamp techniques, e.g., the "cell-attached" mode, the "inside-out" mode, and the "whole cell" mode (see, e.g., Ackerman et al., New Engl. J. Med. 336:1575-1595, 1997). Whole cell currents can be determined using standard methodology such as that described by Hamil et al., Pflugers. Archiv. 391:185 (1981).

Channel activity is also conveniently assessed by measuring changes in intracellular ion levels, i.e., sodium or lithium. Such methods are exemplified herein. For example, sodium flux can be measured by assessment of the uptake of radiolabeled sodium or by using suitable fluorescent dyes. In a typical microfluorimetry assay, a dye which undergoes a change in fluorescence upon binding a single sodium ion, is loaded into the cytosol of ENaC-expressing cells. Upon exposure to ENaC agonist, an increase in cytosolic sodium is reflected by a change in fluorescence that occurs when sodium is bound.

The activity of ENaC polypeptides can in addition to these preferred methods also be assessed using a variety of other in vitro and in vivo assays to determine functional, chemical, and physical effects, e.g., measuring the binding of ENaC to other molecules, including peptides, small organic molecules, and lipids; measuring ENaC protein and/or RNA levels, or measuring other aspects of ENaC polypeptides, e.g., transcription levels, or physiological changes that affects ENaC activity. When the functional consequences are determined using intact cells or animals, one can also measure a variety of effects such as changes in cell growth or pH changes or changes in intracellular second messengers such as IP3, cGMP, or cAMP, or components or regulators of the phospholipase C signaling pathway. Such assays can be used to test for both activators and inhibitors of ENaC proteins. Modulators thus identified are useful for, e.g., many diagnostic and therapeutic applications.

In Vitro Assays

Assays to identify compounds with ENaC modulating activity are preferably performed in vitro. The assays herein preferably use full length ENaC protein or a variant thereof. This protein can optionally be fused to a heterologous protein to form a chimera. In the assays exemplified herein, cells which express the full-length ENaC polypeptide are used in high throughput assays are used to identify compounds that modulate wild-type and mutant ENaCs. Alternatively, purified recombinant or naturally occurring ENaC protein can be used in the in vitro methods of the invention. In addition to purified ENaC protein or fragment thereof, the recombinant or naturally occurring ENaC protein can be part of a cellular lysate or a cell membrane. As described below, the binding assay can be either solid state or soluble. Preferably, the protein, fragment thereof or membrane is bound to a solid support, either covalently or non-covalently. Often, the in vitro assays of the invention are ligand binding or ligand affinity assays, either non-competitive or competitive (with known extracellular ligands such as menthol). Other in vitro assays include measuring changes in spectroscopic (e.g., fluorescence, absorbance, refractive index), hydrodynamic (e.g., shape), chromatographic, or solubility properties for the protein.

Preferably, a high throughput binding assay is performed in which the ENaC protein is contacted with a potential modulator and incubated for a suitable amount of time. A wide variety of modulators can be used, as described below, including small organic molecules, peptides, antibodies, and ENaC ligand analogs. A wide variety of assays can be used to identify ENaC-modulator binding, including labeled protein-protein binding assays, electrophoretic mobility shifts, immunoassays, enzymatic assays such as phosphorylation assays, and the like. In some cases, the binding of the candidate modulator is determined through the use of competitive binding assays, where interference with binding of a known ligand is measured in the presence of a potential modulator. Ligands for the ENaC family are known. Also amiloride and phenamil are known to inhibit ENaC function. In such assays the known ligand is bound first, and then the desired compound i.e., putative enhancer is added. After the ENaC protein is washed, interference with binding, either of the potential modulator or of the known ligand, is determined. Often, either the potential modulator or the known ligand is labeled.

In addition, high throughput functional genomics assays can also be used to identify modulators of cold sensation by identifying compounds that disrupt protein interactions between ENaC and other proteins to which it binds. Such assays can, e.g., monitor changes in cell surface marker expression, changes in intracellular calcium, or changes in membrane currents using either cell lines or primary cells. Typically, the cells are contacted with a cDNA or a random peptide library (encoded by nucleic acids). The cDNA library can comprise sense, antisense, full length, and truncated cDNAs. The peptide library is encoded by nucleic acids. The effect of the cDNA or peptide library on the phenotype of the cells is then monitored, using an assay as described above. The effect of the cDNA or peptide can be validated and distinguished from somatic mutations, using, e.g., regulatable expression of the nucleic acid such as expression from a tetracycline promoter. cDNAs and nucleic acids encoding peptides can be rescued using techniques known to those of skill in the art, e.g., using a sequence tag.

Proteins interacting with the ENaC protein encoded by the cDNA can be isolated using a yeast two-hybrid system, mammalian two hybrid system, or phage display screen, etc. Targets so identified can be further used as bait in these assays to identify additional components that may interact with the ENaC channel which members are also targets for drug development (see, e.g., Fields et al., Nature 340:245 (1989); Vasavada et al., Proc. Nat'l Acad. Sci. USA 88:10686 (1991); Fearon et al., Proc. Nat'l Acad. Sci. USA 89:7958 (1992); Dang et al., Mol. Cell. Biol. 11:954 (1991); Chien et al., Proc. Nat'l Acad. Sci. USA 9578 (1991); and U.S. Pat. Nos. 5,283,173, 5,667,973, 5,468,614, 5,525,490, and 5,637,463).

Cell-Based in Vivo Assays

In preferred embodiments, wild-type and mutant ENaC subunit proteins are expressed in a cell, and functional, e.g., physical and chemical or phenotypic, changes are assayed to identify ENaC modulators that modulate ENaC function or which restore the function of mutant ENaCs, e.g., those having impaired gating function. Cells expressing ENaC proteins can also be used in binding assays. Any suitable functional effect can be measured, as described herein. For example, changes in membrane potential, changes in intracellular lithium or sodium levels, and ligand binding are all suitable assays to identify potential modulators using a cell based system. Suitable cells for such cell based assays include both primary cells and recombinant cell lines engineered to express a ENaC protein. The ENaC proteins therefore can be naturally occurring or recombinant. Also, as described above, fragments of ENaC proteins or chimeras with ion channel activity can be used in cell based assays. For example, a transmembrane domain of a ENaC protein can be fused to a cytoplasmic domain of a heterologous protein, preferably a heterologous ion channel protein. Such a chimeric protein would have ion channel activity and could be used in cell based assays of the invention. In another embodiment, a domain of the ENaC protein, such as the extracellular or cytoplasmic domain, is used in the cell-based assays of the invention.

In another embodiment, cellular ENaC polypeptide levels can be determined by measuring the level of protein or mRNA. The level of ENaC protein or proteins related to ENaC ion channel activation are measured using immunoassays such as western blotting, ELISA and the like with an antibody that selectively binds to the ENaC polypeptide or a fragment thereof. For measurement of mRNA, amplification, e.g., using PCR, LCR, or hybridization assays, e.g., northern hybridization, RNAse protection, dot blotting, are preferred. The level of protein or mRNA is detected using directly or indirectly labeled detection agents, e.g., fluorescently or radioactively labeled nucleic acids, radioactively or enzymatically labeled antibodies, and the like, as described herein.

Alternatively, ENaC expression can be measured using a reporter gene system. Such a system can be devised using a ENaC protein promoter operably linked to a reporter gene such as chloramphenicol acetyltransferase, firefly luciferase, bacterial luciferase, β-galactosidase and alkaline phosphatase. Furthermore, the protein of interest can be used as an indirect reporter via attachment to a second reporter such as red or green fluorescent protein (see, e.g., Mistili & Spector, Nature Biotechnology 15:961-964 (1997)). The reporter construct is typically transfected into a cell. After treatment with a potential modulator, the amount of reporter gene transcription, translation, or activity is measured according to standard techniques known to those of skill in the art.

In another embodiment, a functional effect related to signal transduction can be measured. An activated or inhibited ENaC will alter the properties of target enzymes, second messengers, channels, and other effector proteins. The examples include the activation of phospholipase C and other signaling systems. Downstream consequences can also be examined such as generation of diacyl glycerol and IP3 by phospholipase C.

Assays for ENaC activity include cells that are loaded with ion or voltage sensitive dyes to report activity, e.g., by observing sodium influx or intracellular sodium release. Assays for determining activity of such receptors can also use known agonists and antagonists for ENaC receptors as negative or positive controls to assess activity of tested compounds. In assays for identifying modulatory compounds (e.g., agonists, antagonists), changes in the level of ions in the cytoplasm or membrane voltage will be monitored using an ion sensitive or membrane voltage fluorescent indicator, respectively. Among the ion-sensitive indicators and voltage probes that may be employed are those disclosed in the Molecular Probes 1997 Catalog. Radiolabeled ion flux assays or a flux assay coupled to atomic absorption spectroscopy can also be used.

Animal Models

Animal models also find potential use in screening for modulators of ENaC activity. Similarly, transgenic animal technology including gene knockout technology, for example as a result of homologous recombination with an appropriate gene targeting vector, or gene overexpression, will result in the absence or increased expression of the ENaC protein. The same technology can also be applied to make knock-out cells. When desired, tissue-specific expression or knockout of the ENaC protein may be necessary. Transgenic animals generated by such methods find use as animal models of ENaC related responses.

Knock-out cells and transgenic mice can be made by insertion of a marker gene or other heterologous gene into an endogenous ENaC gene site in the mouse genome via homologous recombination. Such mice can also be made by substituting an endogenous ENaC with a mutated version of the ENaC gene, or by mutating an endogenous ENaC, e.g., by exposure to known mutagens.

A DNA construct is introduced into the nuclei of embryonic stem cells. Cells containing the newly engineered genetic lesion are injected into a host mouse embryo, which is re-implanted into a recipient female. Some of these embryos develop into chimeric mice that possess germ cells partially derived from the mutant cell line. Therefore, by breeding the chimeric mice it is possible to obtain a new line of mice containing the introduced genetic lesion (see, e.g., Capecchi et al., Science 244:1288 (1989)). Chimeric targeted mice can be derived according to Hogan et al., Manipulating the Mouse Embryo: A Laboratory Manual (1988) and Teratocarcinomas and Embryonic Stem Cells: A Practical Approach (Robertson, ed., 1987).

Candidate ENaC Modulators

The compounds tested as modulators of ENaC protein can be any small organic molecule, or a biological entity, such as a protein, e.g., an antibody or peptide, a sugar, a nucleic acid, e.g., an antisense oligonucleotide or a ribozyme, or a lipid. Alternatively, modulators can be genetically altered versions of an ENaC protein. Typically, test compounds will be small organic molecules, peptides, lipids, and lipid analogs. In one embodiment, the compound is a menthol analog, either naturally occurring or synthetic.

Essentially any chemical compound can be used as a potential modulator or ligand in the assays of the invention, although most often compounds can be dissolved in aqueous or organic (especially DMSO-based) solutions are used. The assays are designed to screen large chemical libraries by automating the assay steps and providing compounds from any convenient source to assays, which are typically run in parallel (e.g., in microtiter formats on microtiter plates in robotic assays). It will be appreciated that there are many suppliers of chemical compounds, including Sigma (St. Louis, Mo.), Aldrich (St. Louis, Mo.), Sigma-Aldrich (St. Louis, Mo.), Fluka Chemika-Biochemica Analytika (Buchs Switzerland) and the like.

In one preferred embodiment, high throughput screening methods involve providing a combinatorial small organic molecule or peptide library containing a large number of potential therapeutic compounds (potential modulator or ligand compounds). Such "combinatorial chemical libraries" or "ligand libraries" are then screened in one or more assays, as described herein, to identify those library members (particular chemical species or subclasses) that display a desired characteristic activity. The compounds thus identified can serve as conventional "lead compounds" or can themselves be used as potential or actual therapeutics.

A combinatorial chemical library is a collection of diverse chemical compounds generated by either chemical synthesis or biological synthesis, by combining a number of chemical "building blocks" such as reagents. For example, a linear combinatorial chemical library such as a polypeptide library is formed by combining a set of chemical building blocks (amino acids) in every possible way for a given compound length (i.e., the number of amino acids in a polypeptide compound). Millions of chemical compounds can be synthesized through such combinatorial mixing of chemical building blocks.

Preparation and screening of combinatorial chemical libraries is well known to those of skill in the art. Such combinatorial chemical libraries include, but are not limited to, peptide libraries (see, e.g., U.S. Pat. No. 5,010,175, Furka, Int. J. Pept. Prot. Res. 37:487493 (1991) and Houghton et al., Nature 354:84-88 (1991)). Other chemistries for generating chemical diversity libraries can also be used. Such chemistries include, but are not limited to: peptoids (e.g., PCT Publication No. WO 91/19735), encoded peptides (e.g., PCT Publication No. WO 93/20242), random bio-oligomers (e.g., PCT Publication No. WO 92/00091), benzodiazepines (e.g., U.S. Pat. No. 5,288,514), diversomers such as hydantoins, benzodiazepines and dipeptides (Hobbs et al., Proc. Nat. Acad. Sci. USA 90:6909-6913 (1993)), vinylogous polypeptides (Hagihara et al., J. Amer. Chem. Soc. 114:6568 (1992)), nonpeptidal peptidomimetics with glucose scaffolding (Hirschmann et al., J. Amer. Chem. Soc. 114:9217-9218 (1992)), analogous organic syntheses of small compound libraries (Chen et al., J. Amer. Chem. Soc. 116:2661 (1994)), oligocarbamates (Cho et al., Science 261:1303 (1993)), and/or peptidyl phosphonates (Campbell et al., J. Org. Chem. 59:658 (1994)), nucleic acid libraries (see Ausubel, Berger and Sambrook, all supra), peptide nucleic acid libraries (see, e.g., U.S. Pat. No. 5,539,083), antibody libraries (see, e.g., Vaughn et al., Nature Biotechnology, 14(3):309-314 (1996) and PCT/US96/10287), carbohydrate libraries (see, e.g., Liang et al., Science, 274: 1520-1522 (1996) and U.S. Pat. No. 5,593,853), small organic molecule libraries (see, e.g., benzodiazepines, Baum C & E N, January 18, page 33 (1993); isoprenoids, U.S. Pat. No. 5,569,588; thiazolidinones and metathiazanones, U.S. Pat. No. 5,549,974; pyrrolidines, U.S. Pat. Nos. 5,525,735 and 5,519,134; morpholino compounds, U.S. Pat. No. 5,506, 337; benzodiazepines, U.S. Pat. No. 5,288,514, and the like).

Devices for the preparation of combinatorial libraries are commercially available (see, e.g., 357 MPS, 390 MPS, Advanced Chem Tech, Louisville Ky., Symphony, Rainin, Woburn, Mass., 433A Applied Biosystems, Foster City, Calif., 9050 Plus, Millipore, Bedford, Mass.). In addition, numerous combinatorial libraries are themselves commercially available (see, e.g., ComGenex, Princeton, N.J., Asinex, Moscow, Ru, Tripos, Inc., St. Louis, Mo., Chem-Star, Ltd, Moscow, RU, 3D Pharmaceuticals, Exton, Pa., Martek Biosciences, Columbia, Md.). C. Solid State and Soluble High Throughput Assays Additionally soluble assays can be effected using a ENaC protein, or a cell or tissue expressing a ENaC protein, either naturally occurring or recombinant. Still alternatively, solid phase based in vitro assays in a high throughput format can be effected, where the ENaC protein or fragment thereof, such as the cytoplasmic domain, is attached to a solid phase substrate. Any one of the assays described herein can be adapted for high throughput screening, e.g., ligand binding, calcium flux, change in membrane potential, etc.

In the high throughput assays of the invention, either soluble or solid state, it is possible to screen several thousand different modulators or ligands in a single day. This methodology can be used for ENaC proteins in vitro, or for cell-based or membrane-based assays comprising an ENaC protein. In particular, each well of a microtiter plate can be used to run a separate assay against a selected potential modulator, or, if concentration or incubation time effects are to be observed, every 5-10 wells can test a single modulator. Thus, a single standard microtiter plate can assay about 100 (e.g., 96) modulators. If 1536 well plates are used, then a single plate can easily assay from about 100-about 1500 different compounds. It is possible to assay many plates per day; assay screens for up to about 6,000, 20,000, 50,000, or more than 100,000 different compounds are possible using the integrated systems of the invention.

For a solid state reaction, the protein of interest or a fragment thereof, e.g., an extracellular domain, or a cell or membrane comprising the protein of interest or a fragment thereof as part of a fusion protein can be bound to the solid state component, directly or indirectly, via covalent or non covalent linkage e.g., via a tag. The tag can be any of a variety of components. In general, a molecule which binds the tag (a tag binder) is fixed to a solid support, and the tagged molecule of interest is attached to the solid support by interaction of the tag and the tag binder.

A number of tags and tag binders can be used, based upon known molecular interactions well described in the literature. For example, where a tag has a natural binder, for example, biotin, protein A, or protein G, it can be used in conjunction with appropriate tag binders (avidin, streptavidin, neutravidin, the Fc region of an immunoglobulin, etc.) Antibodies to molecules with natural binders such as biotin are also widely available and appropriate tag binders; see, SIGMA Immunochemicals 1998 catalogue SIGMA, St. Louis Mo.).

Similarly, any haptenic or antigenic compound can be used in combination with an appropriate antibody to form a tag/tag binder pair. Thousands of specific antibodies are commercially available and many additional antibodies are described in the literature. For example, in one common configuration, the tag is a first antibody and the tag binder is a second antibody which recognizes the first antibody. In addition to antibody-antigen interactions, receptor-ligand interactions are also appropriate as tag and tag-binder pairs. For example, agonists and antagonists of cell membrane receptors (e.g., cell receptor-ligand interactions such as transferrin, c-kit, viral receptor ligands, cytokine receptors, chemokine receptors, interleukin receptors, immunoglobulin receptors and antibodies, the cadherin family, the integrin family, the selectin family, and the like; see, e.g., Pigott & Power, The Adhesion Molecule Facts Book I (1993). Similarly, toxins and venoms, viral epitopes, hormones (e.g., opiates, steroids, etc.), intracellular receptors (e.g. which mediate the effects of various small ligands, including steroids, thyroid hormone, retinoids and vitamin D; peptides), drugs, lectins, sugars, nucleic acids (both linear and cyclic polymer configurations), oligosaccharides, proteins, phospholipids and antibodies can all interact with various cell receptors.

Synthetic polymers, such as polyurethanes, polyesters, polycarbonates, polyureas, polyamides, polyethyleneimines, polyarylene sulfides, polysiloxanes, polyimides, and polyacetates can also form an appropriate tag or tag binder. Many other tag/tag binder pairs are also useful in assay systems described herein, as would be apparent to one of skill upon review of this disclosure.

Common linkers such as peptides, polyethers, and the like can also serve as tags, and include polypeptide sequences, such as poly gly sequences of between about 5 and 200 amino acids. Such flexible linkers are known to persons of skill in the art. For example, poly(ethelyne glycol) linkers are available from Shearwater Polymers, Inc. Huntsville, Ala. These linkers optionally have amide linkages, sulfhydryl linkages, or heterofunctional linkages.

Tag binders are fixed to solid substrates using any of a variety of methods currently available. Solid substrates are commonly derivatized or functionalized by exposing all or a portion of the substrate to a chemical reagent which fixes a chemical group to the surface which is reactive with a portion of the tag binder. For example, groups which are suitable for attachment to a longer chain portion would include amines, hydroxyl, thiol, and carboxyl groups. Aminoalkylsilanes and hydroxyalkylsilanes can be used to functionalize a variety of surfaces, such as glass surfaces. The construction of such solid phase biopolymer arrays is well described in the literature. See, e.g., Merrifield, J. Am. Chem. Soc. 85:2149-2154 (1963) (describing solid phase synthesis of, e.g., peptides); Geysen et al., J. Immunol. Meth. 102:259-274 (1987) (describing synthesis of solid phase components on pins); Frank & Doring, Tetrahedron 44:6031-6040 (1988) (describing synthesis of various peptide sequences on cellulose disks); Fodor et al., Science, 251:767-777 (1991); Sheldon et al., Clinical Chemistry 39(4):718-719 (1993); and Kozal et al., Nature Medicine 2(7):753-759 (1996) (all describing arrays of biopolymers fixed to solid substrates). Non-chemical approaches for fixing tag binders to substrates include other common methods, such as heat, cross-linking by UV radiation, and the like.

Having described the invention supra, the examples provided infra further illustrate some preferred embodiments of the invention. These examples are provided only for purposes of illustration and should not be construed as limiting the subject invention.

Practical Applications of the Invention

Compounds which modulate, preferably enhance the activity of delta hENaC have important implications in modulation of human salty taste.

Compounds which activate hENaC in taste papillae on the tongue can be used to enhance salt sensation by promoting Na$^+$ transport into taste bud cells (Kretz et al., J Histochem Cytochem., 4751-64 (1999); Lin et al., J Comp. Neurol. 405:406420 (1999). This has obvious consumer applications in improving the taste and palatability of low salt foods and beverages.

The following examples were effected using the materials and methods described supra. These examples are put forth so as to provide those of ordinary skill in the art with a complete disclosure and description of how to make and use the subject invention, and are not intended to limit the scope of what is regarded as the invention.

EXAMPLES

Example 1

Comparison of Delta Beta Gamma hENaC and Alpha Beta Gamma mENaC Function in Oocytes Oocytes described above expressing delta beta gamma human ENaC and alpha beta gamma human ENaC function in oocytes were produced using the materials and methods described supra and ENaC sequences provided in the Sequence Listing preceding the claims. These oocytes were then contacted with amiloride in the absence and presence of a proprietary ENaC enhancer identified by Senomyx. As shown in FIG. 1A, representative amiloride inhibition curves for alpha beta gamma hENaC (n equals 16) and delta beta gamma hENaC (n equals 10) were obtained. Half-maximal inhibition of delta beta gamma hENaC required about 25-fold higher concentrations of amiloride compared with alpha beta gamma mENaC. As shown in FIG. 1B the representative proprietary enhancer compound identified as 6363969 resulted in the dose-response curves for alpha beta gamma hENaC (n equals 46) and delta beta gamma hENaC (n equals 11) shown therein. The proprietary compound activated delta beta gamma hENaC with similar efficacy and potency as alpha beta gamma hENaC. The experiments testing compounds with delta beta gamma hENaC used 10 micromolar amiloride whereas experiments testing compounds with alpha beta gamma hENaC used 1 micromolar amiloride, concentrations yielding greater than 90% hENaC inhibition, to calculate % hENaC activation values.

Example 2

Representative Trace Results

The results of other electrophysiological experiments are also shown in FIGS. 2A and 2B. Representative traces of oocytes expressing alpha beta gamma hENaC are shown in FIG. 2A (top traces) and FIG. 2B contains results for delta beta gamma hENaC (bottom traces) and stimulated with amiloride (1 micromolar for alpha ENaC and 10 micromolar for delta ENaC) and further contacted with the proprietary enhancer compound 6363969 (1 micromolar concentration). This proprietary compound as shown in FIGS. 2A and 2B was found to strongly activate both alpha and delta subunit containing hENaC channels. The trace results show current (uA) on the y-axis as a function of time (sec) on the x-axis. As shown from the results in FIGS. 2A and 2B the results for both the alpha and the delta containing ENaC are similar.

Example 3

Taste Cell Specific Expression of Delta ENaC Shown by PCR

In order to confirm the potential role of the delta ENaC and other ENaC subunits in taste perception, particularly salty taste, 73 sodium channels were screened from the monkey genome (*Macaca fascicularis* or cynomolgus macaque) for expression in monkey circumvallate (CV) papilla taste cells but not in control lingual epithelial cells by PCR. Both taste and lingual cells wee isolated by laser capture microdissection. These PCR experiments identified numerous taste-specific genes as anticipated including the G-protein gustducin, a gene encoding a polypeptide component of the sweet receptor, T1R2, the ion channel TRPM5

Figure 3:
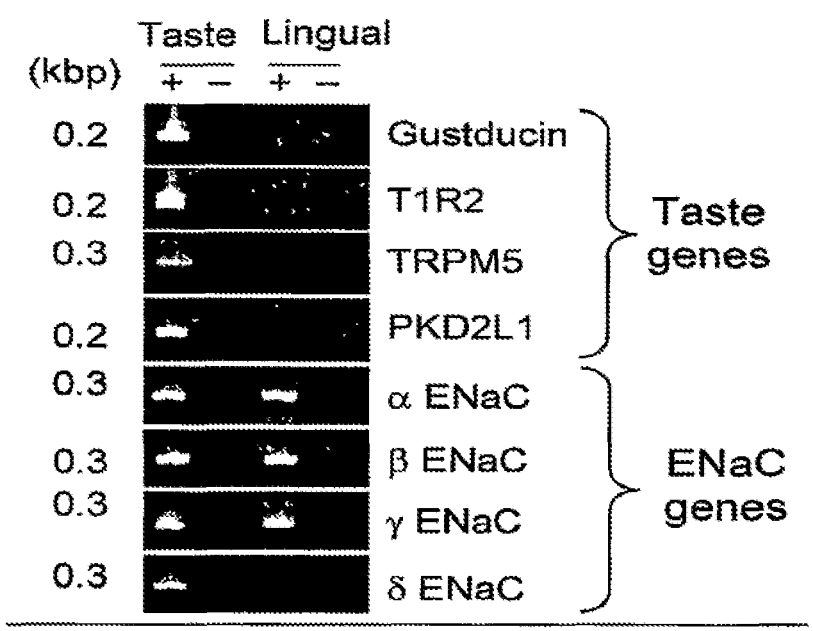
FIG. 3 shows taste-cell specific expression of delta ENaC in monkey CV taste tissue by PCR screening. Monkey PCR primers specific for each gene were used to amplify cDNA from purified CV taste or lingual cells isolated by laser capture microdissection. '+' indicates that reverse transcription was performed and cDNA was added to the PCR reaction; '−' indicates no reverse transcription was performed and no cDNA was added to the PCR reaction. Note that delta ENaC is only present in taste cells but not lingual cells.

(expressed in sweet, bitter, and umami cells) and PKD2L1 (an ion channel expressed in sour cells). Of relevance to the present invention the inventors identified delta ENaC as a taste-specific gene whereas alpha, beta and gamma ENaC were not taste-cell specific but rather were expressed in both taste and lingual cells (FIG. 3). As shown therein monkey PCR primers specific for each gene were used to amplify cDNA from purified circumvallate (CV) taste or lingual cells isolated by laser capture microdissection. In FIG. 3 a '+' indicates that reverse transcription was performed and that cDNA was added to the PCR reaction. A '−' indicates that no reverse transcription was performed and that no cDNA was added to the PCR reaction. As shown in FIG. 3 delta ENaC is only present in taste cells and is not expressed in lingual cells. DNA sequencing analysis further confirmed the sequences of all four ENaC genes in taste cells.

Example 4

Taste Cell Specific Expression Shown by in Situ Hybridization

Figure 4:
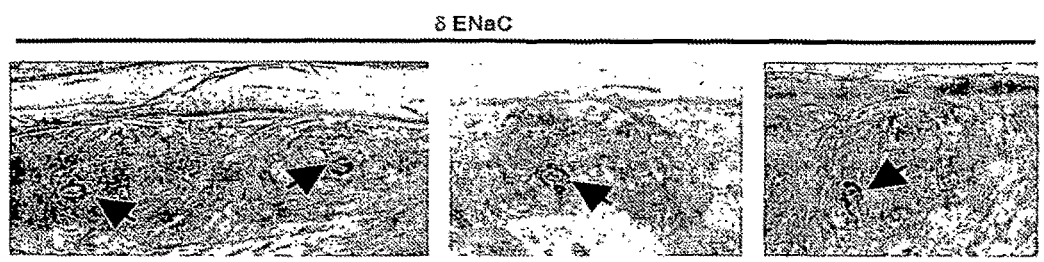
FIG. 4 contains the results of in situ hybridization experiments showing delta ENaC mRNA expression in a subset of monkey CV taste cells. Red arrows denote cells expressing delta ENaC mRNA (colored blue) in taste buds. Tissue sections were labeled with an antisense cRNA probe. Note that only a subset of taste cells express delta ENaC mRNA.

Histology experiments were also performed to determine whether delta ENaC is expressed in a subset of taste receptor cells as would be expected for a salt taste receptor target. Using in situ hybridization to label delta ENaC mRNA, it was determined that delta ENaC was expressed in a subset of monkey CV cells (See FIG. 4). As shown therein the cells identified by the arrows denote taste cells expressing delta ENaC. Only a subset of taste cells express the delta ENaC protein, as expected for a salt receptor.

Additionally, Table 1 below contains a summary of the results of similar electrophysiological experiments conducted using the delta beta gamma and alpha beta gamma hENaC which were activated by various enhancer chemical classes. These assays similarly revealed that the alpha beta gamma and delta beta gamma ENaC channels are equally stimulated by different enhancer classes. [These experiments used 5-7 oocytes per experiment.] Based on these results, it is anticipated that delta ENaC enhancers identified using this or similar cell-based assays may be used to modulate salty taste.

TABLE 1

Summary of αβγ and δβγ hENaC activation by various enhancer chemical classes.

| Compound | % Enhance αβγ | % Enhance δβγ | EC50 (uM) αβγ | EC50(uM) δβγ |
|---|---|---|---|---|
| 6363969 (1 uM) | 359 +/− 67 | 348 +/− 94 | 0.47 | 0.32 |
| 6028354 (3 uM) | 376 +/− 43 | 219 +/− 54 | 1.90 | 1.02 |
| UGI (100 uM) | 29 +/− 12 | 25 +/− 7 | ND | ND |
| Choline Cl | 53 +/− 17 | 52 +/− 5 | ND | ND |

Alpha beta gamma and delta beta gamma ENaC channels are equally stimulated by different enhancer classes. N = 5-7 oocytes per experiment

REFERENCES

All the references cited in this application are incorporated by reference in their entirety herein.

SEQUENCE LISTING OF ENaC DNA AND PROTEIN SEQUENCES

SEQUENCE NO: 1:
Human Delta ENaC DNA Sequence:

atggctgagcaccgaagcatggacgggagaatggaagcagccacacgggggggctctcacctccaggctgcagcccagac gcccccaggccggggccaccatcagcaccaccaccaccacccaaggaggggcaccaggagggggctggtggagctgcccg cctcgttccgggagctgctcaccttcttctgcaccaatgccaccatccacggcgccatccgcctggtctgctcccgcggg aaccgcctcaagacgacgtcctgggggctgctgtccctgggagccctggtcgcgctctgctggcagctggggctcctctt tgagcgtcactggcaccgccggtcctcatggccgtctctgtgcactcggagcgcaagctgctcccgctggtcaccctgt gtgacgggaacccacgtcggccgagtccggtcctccgccatctggagctgctggacgagtttgccagggagaacattgac tccctgtacaacgtcaacctcagcaaaggcagagccgccctctccgccactgtccccgccacgagccccccttccacct ggaccgggagatccgtctgcagaggctgagccactcgggcagccgggtcagagtggggttcagactgtgcaacagcacgg gcggcgactgcttttaccgaggctacacgtcaggcgtggcggctgtccaggactggtaccacttccactatgtggatatc ctggccctgctgcccgcggcatggaggacagccacggagccaggacggccacttcgtcctctcctgcagttacgatgg cctggactgccaggcccgacagttccggaccttccaccaccccacctacggcagctgctacacggtcgatggcgctgga cagctcagcgccccggcatcacccacggagtcggcctggtcctcagggttgagcagcagcctcacctccctctgctgtcc acgctggccggcatcagggtcatggttcacggccgtaaccacacgcccttcctggggcaccacagcttcagcgtccggcc agggacggaggccaccatcagcatccgagaggacgaggtgcaccggctcgggagccctacggccactgcaccgccggcg gggaaggcgtggaggtggagctgctacacaacacctcctacaccaggcaggcctgcctggtgtcctgcttccagcaActg atggtggagacctgctcctgtggctactacctccaccctctgccggcgggggctgagtactgcagctctgcccggcaccc tgcctggggacactgcttctaccgcctctaccaggacctggagacccaccggctcccctgtacctcccgctgcccaggc cctgcagggagtctgcattcaagctctccactgggacctccaggtggccttccgccaagtcagctggatggactctggcc SEQUENCE LISTING OF ENaC DNA AND PROTEIN SEQUENCES acgctaggtgaacaggggctgccgcatcagagccacagacagaggagcagcctggccaaaatcaacatcgtctaccagga gctcaactaccgctcagtggaggaggcgcccgtgtactcggtgccgcagctgctctcGgccatgggcagcctctGcagcc tgtggtttggggcctccgtcctctccctcctggagctcctggagctgctgctcgatgcttctgccctcaccctggtgcta ggcggccgccggctccgcagggcgtggttctcctggcccagagccagccctgcctcaggggcgtccagcatcaagccaga ggccagtcagatgcccccgcctgcaggcggcacgtcagatgacccggagcccagcgggcctcatctcccacgggtgatgc ttccaggggttctggcgggagtTtcagccgaagagagctgggctgggccccagccccttgagactctggacacctga SEQUENCE NO: 2:
Human Delta ENaC Protein Sequence:

MAEHRSMDGRMEAATRGGSHLQAAAQTPPRPGPPSAPPPPPKEGHQEGLVELPASF

RELLTFFCTNATIHGAIRLVCSRGNRLKTTSWGLLSLGALVALCWQLGLLFERHWHR

PVLMAVSVHSERKLLPLVTLCDGNPRRPSPVLRHLELLDEFARENIDSLYNVNLSKGR

AALSATVPRHEPPFHLDREIRLQRLSHSGSRVRVGFRLCNSTGGDCFYRGYTSGVAAV

QDWYHFHYVDILALLPAAWEDSHGSQDGHFVLSCSYDGLDCQARQFRTFHHPTYG

SCYTVDGVWTAQRPGITHGVGLVLRVEQQPHLPLLSTLAGIRVMVHGRNHTPFLGH

HSFSVRPGTEATISIREDEVHRLGSPYGHCTAGGEGVEVELLHNTSYTRQACLVSCFQ

QLMVETCSCGYYLHPLPAGAEYCSSARHPAWGHCFYRLYQDLETHRLPCTSRCPRPC

RESAFKLSTGTSRWPSAKSAGWTLATLGEQGLPHQSHRQRSSLAKINIVYQELNYRSV

EEAPVYSVPQLLSAMGSLcSLWFGASVLSLLELLELLLDASALTLVLGGRRLRRAWFS

WPRASPASGASSIKPEASQMPPPAGGTSDDPEPSGPHLPRVMLPGVLAGVSAEESWA

GPQPLETLDT

SEQUENCE NO: 3:
Human Alpha ENaC DNA Sequence:

atggaggggaacaagctggaggagcaggactctagccctccacagtccactccagggctcatgaaggggaacaagcgtga ggagcaggggctgggccccgaacctgcggcgccccagcagcccacgcgcggaggaggaggccctgatcgagttccaccgct cctaccgagagctcttcgagttcttctgcaacaacaccaccatccacggcgccatccgcctggtgtgctcccagcacaac cgcatgaagacggccttctgggcagtgctgtggctctgcacctttggcatgatgtactggcaattcggcctgcttttcgg agagtacttcagctaccccgtcagcctcaacatcaacctcaactcggacaagctcgtcttccccgcagtgaccatctgca ccctcaatccctacaggtaccggaaattaaagaggagctggaggagctggaccgcatcacagagcagacgctctttgac ctgtacaaatacagctccttcaccactctcgtggccggctcccgcagccgtcgcgacctgcgggggactctgccgcaccc cttgcagcgcctgagggtcccgccccgcctcacggggcccgtcgagcccgtagcgtggcctccagcttgcgggacaaca accccaggtggactggaaggactggaagatcggcttccagctgtgcaaccagaacaaatcggactgcttctaccagaca tactcatcaggggtggatgcggtgagggagtggtaccgcttccactacatcaacatcctgtcgaggctgccagagactct gccatccctggaggaggacacgctgggcaacttcatcttcgcctgccgcttcaaccaggtctcctgcaaccaggcgaatt actctcacttccaccacccgatgtatggaaactgctatactttcaatgacaagaacaactccaacctctggatgtcttcc atgcctggaatcaacaacggtctgtccctgatgctgcgcgcagagcagaatgacttcattccccctgctgtccacagtgac tggggcccgggtaatggtgcacgggcaggatgaacctgcctttatggatgatggtggctttaacttgcggcctggcgtgg agacctccatcagcatgaggaaggaaaccctggacagacttggggggcgattatggcgactgcaccaagaatggcagtgat gttcctgttgagaacctttaccccttcaaagtacacacagcaggtgtgtattcactcctgcttccaggagagcatgatcaa ggagtgtggctgtgcctacatcttctatccgcggcccccagaacgtggagtactgtgactacagaaagcacagttcctggg

SEQUENCE LISTING OF ENaC DNA AND PROTEIN SEQUENCES ggtactgctactataagctccaggttgacttctcctcagaccacctgggctgtttcaccaagtgccggaagccatgcagc gtgaccagctaccagctctctgctggttactcacgatggccctcggtgacatcccaggaatgggtcttccagatgctatc gcgacagaacaattacaccgtcaacaacaagagaaatggagtggccaaagtcaacatcttcttcaaggagctgaactaca aaaccaattctgagtctccctctgtcacgatggtcacccctcctgtccaacctgggcagccagtggagcctgtggttcggc tcctcggtgttgtctgtggtggagatggctgagctcgtcttttgacctgctggtcatcatgttcctcatgctgctccgaag gttccgaagccgatactggtctccaggccgagggggcaggggtgctcaggaggtagcctccaccctggcatcctcccctc cttcccacttctgcccccacccatgtctctgtccttgtcccagccaggccctgctccctctccagccttgacagcccct cccctgcctatgccaccctgggcccccgccatctccaggggctctgcagggccagttcctccacctgtcctctggg ggggccctga SEQUENCE NO: 4:
Human Alpha ENaC Protein Sequence:

MEGNKLEEQDSSPPQSTPGLMKGNKREEQGLGPEPAAPQQPTAEEEALIEFHRSYRE

LFEFFCNNTTIHGAIRLVCSQHNRMKTAFWAVLWLCTFGMMYWQFGLLFGEYFSYP

VSLNINLNSDKLVFPAVTICTLNPYRYPEIKEELEELDRITEQTLFDLYKYSSFTTLVAGS

RSRRDLRGTLPHPLQRLRVPPPPHGARRARSVASSLRDNNPQVDWKDWKIGFQLCN

QNKSDCFYQTYSSGVDAVREWYRFHYINILSRLPETLPSLEEDTLGNFIFACRFNQVSC

NQANYSHFHHPMYGNCYTFNDKNNSNLWMSSMPGINNGLSLMLRAEQNDFIPLLS

TVTGARVMVHGQDEPAFMDDGGFNLRPGVETSISMRKETLDRLGGDYGDCTKNGS

DVPVENLYPSKYTQQVCIHSCFQESMIKECGCAYIFYPRPQNVEYCDYRKHSSWGYC

YYKLQVDFSSDHLGCFTKCRKPCSVTSYQLSAGYSRWPSVTSQEWVFQMLSRQNNYT

VNNKRNGVAKVNIFFKELNYKTNSESPSVTMVTLLSNLGSQWSLWFGSSVLSVVEM

AELVFDLLVIMFLMLLRRFRSRYWSPGRGGRGAQEVASTLASSPPSHFCPHPMSLSLS

QPGPAPSPALTAPPPAYATLGPRPSPGGSAGASSSTCPLGGP

SEQUENCE NO: 5:
Human Beta ENaC DNA Sequence:

atgcacgtgaagaagtacctGctgaagggcctgcatcggctgcagaagggccccggctacacgtacaaggagctgctggt gtggtactgcgacaacaccaacacccacggccccaagcgcatcatctgtgaggggcccaagaagaaagccatgtggttcc tgctcaccctgctcttcgccgccctcgtctgctggcagtggggcatcttcatcaggacctacttgagctgggaggtcagc gtctccctctccgtaggcttcaagaccatggacttccccgccgtcaccatctgcaatgctagccccttcaagtattccaa aatcaagcatttgctgaaggacctggatgagctgatggaagctgtcctggagagaatcctggctcctgagctaagccatg ccaatgccaccaggaacctgaacttctccatctggaaccacacaccctggtccttattgatgaacggaaccccaccac cccatggtccttgatctctttggagacaaccacaatggcttaacaagcagctcagcatcagaaaagatctgtaatgccca cgggtgcaaaatggccatgagactatgtagcctcaacaggacccagtgtaccttccggaacttcaccagtgctacccagg cattgacagagtggtacatcctgcaggccaccaacatctttgcacaggtgccacagcaggagctagtagagatgagctac cccggcgagcagatgatcctggcctgccattcggagctgagccctgcaactaccggaacttcacgtccatcttctaccc tcactatggcaactgttacatcttcaactggggcatgacagagaaggcacttccttcggccaaccctggaactgaattcg gcctgaagttgatcctggacataggccaggaagactacgtccccttccttgcgtccacggccggggtcaggctgatgctt cacgagcagaggtcatacccccttcatcagagatgagggcatctacGccatgtcggggacagagacgtccatcggggtact cgtggacaagcttcagcgcatgggggagccctacagcccgtgcaccgtgaatggttctgaggtccccgtccaaaacttct SEQUENCE LISTING OF ENaC DNA AND PROTEIN SEQUENCES

```
acagtgactacaacacgacctactccatccaggcctgtcttcgctcctgcttccaagaccacatgatccgtaactgcaac tgtggccactacctgtacccactGccccgtggggagaaatactgcaacaaccggacttcccagactgggcccattgcta ctcagatctacagatgagcgtggcgcagagagagacctgcattggcatgtgcaaggagtcctgcaatgacacccagtaca agatgaccatctccatggctgactggccttctgaggcctccgaggactggattttccacgtcttgtctcaggagcgggac caaagcaccaatatcaccctgagcaggaagggaattgtcaagctcaacatctActtccaagaatttaactatcgcaccat tgaagaatcagcagccaataacatcgtctggctgctctcgaatctgggtggccagtttggcttctggatgggggggctctg tgctgtgcctcatcgagtttggggagatcatcatcgactttgtgtggatcaccatcatcaagctggtggccttggccaag agcctacggcagcggcgagcccaagccagCtacgctggccaccgcccaccgtggccgagctggtggaggcccacaccaa ctttggcttccagcctgacacggcccccgcagcccaacactgggccctaccccagtgagcaggccctgcccatcccag gcaccccgcccccaactatgactccctgcgtctgcagccgctggacgtcatcgagtctgacagtgagggtgatgccatc taa
```

SEQUENCE NO: 6:
Human Beta ENaC Protein Sequence:

MHVKKYLLKGLHRLQKGPGYTYKELLVWYCDNTNTHGPKRIICEGPKKKAMWFLL

TLLFAALVCWQWGIFIRTYLSWEVSVSLSVGFKTMDFPAVTICNASPFKYSKIKHLLK

DLDELMEAVLERILAPELSHANATRNLNFSIWNHTPLVLIDERNPHHPMVLDLFGD

NHNGLTSSSASEKICNAHGCKMAMRLCSLNRTQCTFRNFTSATQALTEWYILQATNI

FAQVPQQELVEMSYPGEQMILACLFGAEPCNYRNFTSIFYPHYGNCYIFNWGMTEKA

LPSANPGTEFGLKLILDIGQEDYVPFLASTAGVRLMLHEQRSYPFIRDEGIYAMSGTET

SIGVLVDKLQRMGEPYSPCTVNGSEVPVQNFYSDYNTTYSIQACLRSCFQDHMIRNC

NCGHYLYPLPRGEKYCNNRDFPDWAHCYSDLQMSVAQRETCIGMCKESCNDTQYK

MTISMADWPSEASEDWIFHVLSQERDQSTNITLSRKGIVKLNIYFQEFNYRTIEESAAN

NIVWLLSNLGGQFGFWMGGSVLCLIEFGEIIIDFVWITIIKLVALAKSLRQRRAQASYA

GPPPTVAELVEAHTNFGFQPDTAPRSPNTGPYPSEQALPIPGTPPPNYDSLRLQPLDVI

ESDSEGDAI

SEQUENCE NO: 7:
Human Gamma ENaC DNA Sequence:

```
atggcacccggagagaagatcaaagccaaaatcaagaagaatctgcccgtgacgggccctcaggcgccgaccattaaaga gctgatgcggtggtactgcctcaacaccaacacccatggctgtcgccgcatcgtggtgtcccgcggccgtctgcgccgcc tcctctggatcggttcacactgactgccgtggccctcatcctctggcagtgcgccctcctcgtcttctccttctatact gtctcagtttccatcaaagtccacttccggaagctggattttcctgcagtcaccatctgcaacatcaaccctacaagta cagcaccgttcgccaccttctagctgacttggaacaggagaccagagaggccctgaagtccctgtatggctttccagagt cccggaagcgccgagaggcggagtcctggaactccgtctcagagggaaagcagcctagattctcccaccggattccgctg ctgatctttgatcaggatgagaagggcaaggccagggacttcttcacagggAggaagcggaaagtcggcggtagcatcat tcacaaggcttcaaatgtcatgcacatcgagtccaagcaagtggtgggattccaactgtgctcaaatgacacctccgact gtgccacctacaccttcagctcgggaatcaatgccattcaggagtggtataagctacactacatgaacatcatggcacag gtgcctctggagaagaaaatcaacatgagctattctgctgaggagctgctggtgacctgcttctttgatggagtgtcctg tgatgccaggaatttcacgcttttccaccaccgatgcatgggaattgctatactttcaacaacagagaaaatgagacca ttctcagcacctccatgggggggcagcgaatatgggctgcaagtcattttgtacataaaacgaagaggaatacaacccattc
```

SEQUENCE LISTING OF ENaC DNA AND PROTEIN SEQUENCES

```
ctcgtgtcctccactggagctaaggtgatcatccatcggcaggatgagtatcccttcgtcgaagatgtgggaacagagat
tgagacagcaatggtcacctctataggaatgcacctgacagagtccttcaagctgagtgagccctacagtcagtgcacgg
aggacgggagtgacgtgccaatcaggaacatctacaacgctgcctactcgctccagatctgccttcattcatgcttccag
acaaagatggtggagaaatgtgggtgtgcccagtacagccagcctctacctcctgcagccaactactgcaactaccagca
gcaccccaactggatgtattgttactaccaactgcatcgagcctttgtccaggaagagctgggctgccagtctgtgtgca
aggaagcctgcagcttttaaagagtggacactaaccacaagcctggcacaatggccatctgtggtttcggagaagtggttg
ctgcctgttctcacttgggaccaaggccggcaagtaaacaaaaagctcaacaagacagacttgGccaaactcttgatatt
ctacaaagacctgaaccagagatccatcatggagagcccagccaacagtattgagatgcttctgtccaacttcggtggcc
agctgggcctgtggatgagctgctctgttgtctgcgtcatcgagatcatcgaggtcttcttcattgacttcttctctatc
attgcccgccgccagtggcagaaagccaaggagtggtgggcctggaaacaggctcccccatgtccagaagctccccgtag
cccacagggccaggacaatccagccctggatatagacgatgacctacccactttcaactctgctttgcacctgcctccaG
ccctaggaacccaagtgcccggcacaccgcccccaaatacaatccttgcgcttggagagggccttttccaaccagctc
acagatacccagatgctAgatgagctctga
```

SEQUENCE NO: 8:
Human Gamma ENaC Protein Sequence:

MAPGEKIKAKIKKNLPVTGPQAPTIKELMRWYCLNTNTHGCRRIVVSRGRLRRLLWI

GFTLTAVALILWQCALLVFSFYTVSVSIKVHFRKLDFPAVTICNINPYKYSTVRHLLAD

LEQETREALKSLYGFPESRKRREAESWNSVSEGKQPRFSHRIPLLIFDQDEKGKARDFF

TGRKRKVGGSIIHKASNVMHIESKQVVGFQLCSNDTSDCATYTFSSGINAIQEWYKLH

YMNIMAQVPLEKKINMSYSAEELLVTCFFDGVSCDARNFTLFHHPMHGNCYTFNNR

ENETILSTSMGGSEYGLQVILYINEEEYNPFLVSSTGAKVIIHRQDEYPFVEDVGTEIET

AMVTSIGMHLTESFKLSEPYSQCTEDGSDVPIRNIYNAAYSLQICLHSCFQTKMVEKC

GCAQYSQPLPPAANYCNYQQHPNWMYCYYQLHRAFVQEELGCQSVCKEACSFKE

WTLTTSLAQWPSVVSEKWLLPVLTWDQGRQVNKKLNKTDLAKLLIFYKDLNQRSIM

ESPANSIEMLLSNFGGQLGLWMSCSVVCVIEIIEVFFIDFFSIIARRQWQKAKEWWAW

KQAPPCPEAPRSPQGQDNPALDIDDDLPTFNSALHLPPALGTQVPGTPPPKYNTLRL

ERAFSNQLTDTQMLDEL

The invention claimed is:

1. An electrophysiological assay for identifying a compound having potential in vivo application for modulating human salty taste comprising the following:
   (i) contacting a cell that expresses a human epithelial sodium channel ("hENaC") channel containing a delta subunit polypeptide possessing at least 90% sequence identity to the polypeptide identical to the polypeptide of SEQ ID NO:10 with at least one putative hENaC enhancer compound;
   (ii) assaying sodium conductance in the presence and absence of said putative hENaC enhancer; and
   (iii) identifying the compound as a potential salty taste enhancer based on whether it increases sodium conductance.

2. The method of claim 1 which further includes determining the effect on salty taste perception of said compound or a derivative thereof in a human taste test.

3. The method of claim 1 wherein the delta hENaC further comprises human beta and gamma subunits or variants thereof.

4. The method of claim 1 wherein the delta hENaC is expressed in an amphibian oocyte.

5. The method of claim 1 wherein the delta hENaC is expressed in a mammalian cell.

6. The method of claim 1 wherein said electrophysiological assay uses a sodium sensitive dye.

7. The method of claim 1 wherein said assay is a two electrode voltage clamping assay.

8. The method of claim 7 wherein the cell is a Xenopus oocyte or a mammalian cell.

9. The method of claim 8 wherein said mammalian cell is selected from the group consisting of a Swiss3T3, CHO, BHK, NIH3T3, and COS cell.

10. The method of claim 8 wherein the cell is a Xenopus oocyte.

11. The method of claim 1 wherein said assay is a patch clamp assay.

12. The method of claim 6 wherein said dye is selected from the group consisting of voltage-sensitive blue dye, 4-(2-(6-(dibutylamino)-2-naphthalen-yl)ethenyl)-1-(3-sulfopropyl)hydroxide, inner salt, DiSBACC4(2)(bis-(1,2-dibabituric acid)-triethine oxanol), Cc-2-DMPE, 1,2-ditetradecanoyl-sn-glycero-3-phosphoethanolamine, triethylammonium salt and SBFI-AM (1,3-benzenedicrboxylic acid, 4,4-(1,4,10-trioxa-7,13-diazacylopentadecane-7, 13-diyibis(5-methoxy-6,1,2-berizofurandiyl))bis-tetrakis [(acetyloxy)methyl]ester.

13. The method of claim 6 which uses a sodium sensitive dye.

14. The method of claim 1 wherein delta hENaC activity is measured by an ion flux assay.

15. The method of claim 14 which uses atomic absorption spectroscopy to detect ion flux.

16. The method of claim 1 wherein the delta hENaC subunit is expressed under the control of a regulatable promoter.

17. The method of claim 1 which uses a fluorescence plate reader.

18. The method of claim 1 which uses a voltage imaging plate reader.

19. The method of claim 1 wherein the selected compound promotes sodium ion transport into taste bud cells.

20. The method of claim 1 which uses a membrane potential dye selected from the group consisting of voltage-sensitive blue dye, Di-4-ANEPPS (pyridinium, 4-(2-(6-(dibutylamino)-2-naphthalen-yl)ethenyl)-1-(3-sulfopropyl)-hydroxide, inner salt); DiSBACC4(2)(bis-(1.2-dibarbituric acid)-trimethine oxanol); DiSBAC4(3) (bis-(1,3-dibarbituric acid)-trimethine oxanol); CC-2-DPME (1,2-ditetradecanoyl-sn-glycerol-3-phosphoethanolamine, triethylammonium salt) and SBFI-AM (1,3-Benzenedicarboxylic acid, 4,4'-[1,4,10-trioxa-7,13-diazacyclopentadecane-7,13-diylbis(5-methoxy-6,1,2-benzofurandiyl)]bis-tetrakis[(acetyloxy)methyl]ester.

21. The method of claim 1 wherein said cell stably expresses said delta hENaC.

22. The method of claim 1 wherein said cell transiently expresses said delta hENaC.

23. The method of claim 21 wherein ENaC activity is monitored using a sodium sensitive dye.

24. The method of claim 1 wherein delta hENaC activity is assayed in a frog oocyte that expresses said delta hENaC electrophysiologically by patch clamping or two electrode voltage clamping.

25. The method of claim 24 which uses an automatic imaging instrument.

26. The method of claim 25 wherein said instrument is a fluorescence plate reader.

27. The method of claim 25 wherein said instrument is a voltage imaging plate reader.

28. The method of claim 1, wherein said cell is selected from the group consisting of BHK, CHO, COS, monkey L cell, African green monkey kidney cell, Ltk-cell and an oocyte.

29. The method of claim 17, wherein said cell is selected from the group consisting of BHK, CHO, COS, monkey L cell, African green monkey kidney cell, Ltk-cell and an oocyte.

30. The method of claim 1, wherein said delta subunit polypeptide possesses at least 95% sequence identity to the polypeptide identical to SEQ ID NO: 10.

31. The method of claim 1, wherein a nucleic acid encoding said delta subunit polypeptide possesses a single nucleotide polymorphism ("SNP").

* * * * *

SEQUENCE LISTING

<160> NUMBER OF SEQ ID NOS: 10

<210> SEQ ID NO 1
<211> LENGTH: 1917
<212> TYPE: DNA
<213> ORGANISM: Homo sapiens

<400> SEQUENCE: 1

```
atggctgagc accgaagcat ggacgggaga atggaagcag ccacacgggg gggctctcac      60
ctccaggctg cagcccagac gcccccagg ccggggccac catcagcacc accaccacca     120
cccaaggagg ggcaccagga ggggctggtg gagctgcccg cctcgttccg ggagctgctc    180
accttcttct gcaccaatgc caccatccac ggcgccatcc gcctggtctg ctcccgcggg     240
```

```
aaccgcctca agacgacgtc ctgggggctg ctgtccctgg gagccctggt cgcgctctgc    300
tggcagctgg ggctcctctt tgagcgtcac tggcaccgcc cggtcctcat ggccgtctct    360
gtgcactcgg agcgcaagct gctcccgctg gtcaccctgt gtgacgggaa cccacgtcgg    420
ccgagtccgg tcctccgcca tctggagctg ctggacgagt tgccaggga gaacattgac    480
tccctgtaca acgtcaacct cagcaaaggc agagccgccc tctccgccac tgtccccgc    540
cacgagcccc ccttccacct ggaccggag atccgtctgc agaggctgag ccactcgggc    600
agccgggtca gagtggggtt cagactgtgc aacagcacgg gcggcgactg cttttaccga    660
ggctacacgt caggcgtggc ggctgtccag gactggtacc acttccacta tgtggatatc    720
ctggccctgc tgcccgcggc atgggaggac agccacggga gccaggacgg ccacttcgtc    780
ctctcctgca gttacgatgg cctggactgc caggcccgac agttccggac cttccaccac    840
cccacctacg gcagctgcta cacggtcgat ggcgtctgga cagctcagcg ccccggcatc    900
acccacggag tcggcctggt cctcagggtt gagcagcagc ctcacctccc tctgctgtcc    960
acgctggccg gcatcagggt catggttcac ggccgtaacc acacgccctt cctggggcac   1020
cacagcttca gcgtccggcc agggacggag gccaccatca gcatccgaga ggacgaggtg   1080
caccggctcg ggagccccta cggccactgc accgccggcg gggaaggcgt ggaggtggag   1140
ctgctacaca acacctccta caccaggcag gcctgcctgg tgtcctgctt ccagcaactg   1200
atggtggaga cctgctcctg tggctactac ctccaccctc tgccggcggg ggctgagtac   1260
tgcagctctg cccggcaccc tgcctgggga cactgcttct accgcctcta ccaggacctg   1320
gagacccacc ggctcccctg tacctcccgc tgccccaggc cctgcaggga gtctgcattc   1380
aagctctcca ctgggacctc caggtggcct tccgccaagt cagctggatg gactctggcc   1440
acgctaggtg aacaggggct gccgcatcag agccacagac agaggagcag cctggccaaa   1500
atcaacatcg tctaccagga gctcaactac cgctcagtgg aggaggcgcc cgtgtactcg   1560
gtgccgcagc tgctctcggc catgggcagc ctctgcagcc tgtggtttgg ggcctccgtc   1620
ctctccctcc tggagctcct ggagctgctg ctcgatgctt ctgccctcac cctggtgcta   1680
ggcggccgcc ggctccgcag ggcgtggttc tcctggccca gagccagccc tgcctcaggg   1740
gcgtccagca tcaagccaga ggccagtcag atgccccgc ctgcaggcgg cacgtcagat   1800
gacccggagc ccagcgggcc tcatctccca cgggtgatgc ttccagggt tctggcggga   1860
gtttcagccg aagagagctg ggctgggccc cagccccttg agactctgga cacctga      1917
```

<210> SEQ ID NO 2
<211> LENGTH: 638
<212> TYPE: PRT
<213> ORGANISM: Homo sapiens

<400> SEQUENCE: 2

Met Ala Glu His Arg Ser Met Asp Gly Arg Met Glu Ala Ala Thr Arg
1               5                   10                  15

Gly Gly Ser His Leu Gln Ala Ala Ala Gln Thr Pro Pro Arg Pro Gly
            20                  25                  30

Pro Pro Ser Ala Pro Pro Pro Pro Lys Glu Gly His Gln Glu Gly
        35                  40                  45

Leu Val Glu Leu Pro Ala Ser Phe Arg Glu Leu Leu Thr Phe Phe Cys
    50                  55                  60

Thr Asn Ala Thr Ile His Gly Ala Ile Arg Leu Val Cys Ser Arg Gly
65                  70                  75                  80

```
Asn Arg Leu Lys Thr Thr Ser Trp Gly Leu Ser Leu Gly Ala Leu
                 85                  90                  95

Val Ala Leu Cys Trp Gln Leu Gly Leu Leu Phe Glu Arg His Trp His
                100                 105                 110

Arg Pro Val Leu Met Ala Val Ser Val His Ser Glu Arg Lys Leu Leu
                115                 120                 125

Pro Leu Val Thr Leu Cys Asp Gly Asn Pro Arg Arg Pro Ser Pro Val
            130                 135                 140

Leu Arg His Leu Glu Leu Leu Asp Glu Phe Ala Arg Glu Asn Ile Asp
145                 150                 155                 160

Ser Leu Tyr Asn Val Asn Leu Ser Lys Gly Arg Ala Ala Leu Ser Ala
                165                 170                 175

Thr Val Pro Arg His Glu Pro Pro Phe His Leu Asp Arg Glu Ile Arg
                180                 185                 190

Leu Gln Arg Leu Ser His Ser Gly Ser Arg Val Arg Val Gly Phe Arg
            195                 200                 205

Leu Cys Asn Ser Thr Gly Gly Asp Cys Phe Tyr Arg Gly Tyr Thr Ser
            210                 215                 220

Gly Val Ala Ala Val Gln Asp Trp Tyr His Phe His Tyr Val Asp Ile
225                 230                 235                 240

Leu Ala Leu Leu Pro Ala Ala Trp Glu Asp Ser His Gly Ser Gln Asp
                245                 250                 255

Gly His Phe Val Leu Ser Cys Ser Tyr Asp Gly Leu Asp Cys Gln Ala
                260                 265                 270

Arg Gln Phe Arg Thr Phe His His Pro Thr Tyr Gly Ser Cys Tyr Thr
            275                 280                 285

Val Asp Gly Val Trp Thr Ala Gln Arg Pro Gly Ile Thr His Gly Val
            290                 295                 300

Gly Leu Val Leu Arg Val Glu Gln Gln Pro His Leu Pro Leu Leu Ser
305                 310                 315                 320

Thr Leu Ala Gly Ile Arg Val Met Val His Gly Arg Asn His Thr Pro
                325                 330                 335

Phe Leu Gly His His Ser Phe Ser Val Arg Pro Gly Thr Glu Ala Thr
                340                 345                 350

Ile Ser Ile Arg Glu Asp Glu Val His Arg Leu Gly Ser Pro Tyr Gly
            355                 360                 365

His Cys Thr Ala Gly Gly Glu Gly Val Glu Val Glu Leu Leu His Asn
370                 375                 380

Thr Ser Tyr Thr Arg Gln Ala Cys Leu Val Ser Cys Phe Gln Gln Leu
385                 390                 395                 400

Met Val Glu Thr Cys Ser Cys Gly Tyr Tyr Leu His Pro Leu Pro Ala
                405                 410                 415

Gly Ala Glu Tyr Cys Ser Ser Ala Arg His Pro Ala Trp Gly His Cys
                420                 425                 430

Phe Tyr Arg Leu Tyr Gln Asp Leu Glu Thr His Arg Leu Pro Cys Thr
            435                 440                 445

Ser Arg Cys Pro Arg Pro Cys Arg Glu Ser Ala Phe Lys Leu Ser Thr
            450                 455                 460

Gly Thr Ser Arg Trp Pro Ser Ala Lys Ser Ala Gly Trp Thr Leu Ala
465                 470                 475                 480

Thr Leu Gly Glu Gln Gly Leu Pro His Gln Ser His Arg Gln Arg Ser
                485                 490                 495
```

```
Ser Leu Ala Lys Ile Asn Ile Val Tyr Gln Glu Leu Asn Tyr Arg Ser
            500                 505                 510

Val Glu Glu Ala Pro Val Tyr Ser Val Pro Gln Leu Leu Ser Ala Met
        515                 520                 525

Gly Ser Leu Cys Ser Leu Trp Phe Gly Ala Ser Val Leu Ser Leu Leu
    530                 535                 540

Glu Leu Leu Glu Leu Leu Leu Asp Ala Ser Ala Leu Thr Leu Val Leu
545                 550                 555                 560

Gly Gly Arg Arg Leu Arg Arg Ala Trp Phe Ser Trp Pro Arg Ala Ser
                565                 570                 575

Pro Ala Ser Gly Ala Ser Ser Ile Lys Pro Glu Ala Ser Gln Met Pro
            580                 585                 590

Pro Pro Ala Gly Gly Thr Ser Asp Asp Pro Glu Pro Ser Gly Pro His
        595                 600                 605

Leu Pro Arg Val Met Leu Pro Gly Val Leu Ala Gly Val Ser Ala Glu
610                 615                 620

Glu Ser Trp Ala Gly Pro Gln Pro Leu Glu Thr Leu Asp Thr
625                 630                 635

<210> SEQ ID NO 3
<211> LENGTH: 2010
<212> TYPE: DNA
<213> ORGANISM: Homo sapiens

<400> SEQUENCE: 3
```

| | | | | | |
|---|---|---|---|---|---|
| atggagggga | caagctgga | ggagcaggac | tctagccctc | cacagtccac | tccagggctc | 60 |
| atgaagggga | caagcgtga | ggagcagggg | ctgggcccg | aacctgcggc | gccccagcag | 120 |
| cccacggcgg | aggaggaggc | cctgatcgag | ttccaccgct | cctaccgaga | gctcttcgag | 180 |
| ttcttctgca | caacaccac | catccacggc | gccatccgcc | tggtgtgctc | ccagcacaac | 240 |
| cgcatgaaga | cggccttctg | gcagtgctg | tggctctgca | cctttggcat | gatgtactgg | 300 |
| caattcggcc | tgcttttcgg | agagtacttc | agctaccccg | tcagcctcaa | catcaacctc | 360 |
| aactcggaca | agctcgtctt | ccccgcagtg | accatctgca | ccctcaatcc | ctacaggtac | 420 |
| ccggaaatta | agaggagct | ggaggagctg | accgcatca | cagagcagac | gctctttgac | 480 |
| ctgtacaaat | acagctcctt | caccactctc | gtggccggct | cccgcagccg | tcgcgacctg | 540 |
| cgggggactc | tgccgcaccc | cttgcagcgc | ctgagggtcc | cgcccccgcc | tcacggggcc | 600 |
| cgtcgagccc | gtagcgtggc | ctccagcttg | cgggacaaca | accccaggt | ggactggaag | 660 |
| gactggaaga | tcgccttcca | gctgtgcaac | cagaacaaat | cggactgctt | ctaccagaca | 720 |
| tactcatcag | gggtggatgc | ggtgagggag | tggtaccgct | ccactacat | caacatcctg | 780 |
| tcgaggctgc | cagagactct | gccatccctg | gaggaggaca | cgctgggcaa | cttcatcttc | 840 |
| gcctgccgct | tcaaccaggt | ctcctgcaac | caggcgaatt | actctcactt | ccaccaccg | 900 |
| atgtatggaa | actgctatac | tttcaatgac | aagaacaact | ccaacctctg | gatgtcttcc | 960 |
| atgcctggaa | tcaacaacgg | tctgtccctg | atgctgcgcg | cagagcagaa | tgacttcatt | 1020 |
| cccctgctgt | ccacagtgac | tgggccccgg | gtaatggtgc | acgggcagga | tgaacctgcc | 1080 |
| tttatggatg | atggtggctt | taacttgcgg | cctggcgtgg | agacctccat | cagcatgagg | 1140 |
| aaggaaaccc | tggacagact | ggggggcgat | tatggcgact | gcaccaagaa | tggcagtgat | 1200 |
| gttcctgttg | agaacctta | ccctctcaaag | tacacacagc | aggtgtgtat | tcactcctgc | 1260 |
| ttccaggaga | gcatgatcaa | ggagtgtggc | tgtgcctaca | tcttctatcc | gcggccccag | 1320 |

```
aacgtggagt actgtgacta cagaaagcac agttcctggg ggtactgcta ctataagctc    1380
caggttgact tctcctcaga ccacctgggc tgtttcacca agtgccggaa gccatgcagc    1440
gtgaccagct accagctctc tgctggttac tcacgatggc cctcggtgac atcccaggaa    1500
tgggtcttcc agatgctatc gcgacagaac aattacaccg tcaacaacaa gagaaatgga    1560
gtggccaaag tcaacatctt cttcaaggag ctgaactaca aaccaattc tgagtctccc     1620 tctgtcacga tggtcaccct cctgtccaac ctgggcagcc agtggagcct gtggttcggc    1680
tcctcggtgt tgtctgtggt ggagatggct gagctcgtct ttgacctgct ggtcatcatg    1740
ttcctcatgc tgctccgaag gttccgaagc cgatactggt ctccaggccg agggggcagg    1800
ggtgctcagg aggtagcctc caccctggca tcctcccctc cttcccactt ctgcccccac    1860
cccatgtctc tgtccttgtc ccagccaggc cctgctccct ctccagcctt gacagcccct    1920 cccctgcct atgccaccct gggccccgc ccatctccag ggggctctgc aggggccagt      1980
tcctccacct gtcctctggg ggggccctga                                     2010
```

<210> SEQ ID NO 4
<211> LENGTH: 669
<212> TYPE: PRT
<213> ORGANISM: Homo sapiens

<400> SEQUENCE: 4

```
Met Glu Gly Asn Lys Leu Glu Glu Gln Asp Ser Ser Pro Pro Gln Ser
1               5                   10                  15

Thr Pro Gly Leu Met Lys Gly Asn Lys Arg Glu Glu Gln Gly Leu Gly
                20                  25                  30

Pro Glu Pro Ala Ala Pro Gln Gln Pro Thr Ala Glu Glu Glu Ala Leu
            35                  40                  45

Ile Glu Phe His Arg Ser Tyr Arg Glu Leu Phe Glu Phe Phe Cys Asn
        50                  55                  60

Asn Thr Thr Ile His Gly Ala Ile Arg Leu Val Cys Ser Gln His Asn
65                  70                  75                  80

Arg Met Lys Thr Ala Phe Trp Ala Val Leu Trp Leu Cys Thr Phe Gly
                85                  90                  95

Met Met Tyr Trp Gln Phe Gly Leu Leu Phe Gly Glu Tyr Phe Ser Tyr
                100                 105                 110

Pro Val Ser Leu Asn Ile Asn Leu Asn Ser Asp Lys Leu Val Phe Pro
            115                 120                 125

Ala Val Thr Ile Cys Thr Leu Asn Pro Tyr Arg Tyr Pro Glu Ile Lys
        130                 135                 140

Glu Glu Leu Glu Glu Leu Asp Arg Ile Thr Glu Gln Thr Leu Phe Asp
145                 150                 155                 160

Leu Tyr Lys Tyr Ser Ser Phe Thr Thr Leu Val Ala Gly Ser Arg Ser
                165                 170                 175

Arg Arg Asp Leu Arg Gly Thr Leu Pro His Pro Leu Gln Arg Leu Arg
            180                 185                 190

Val Pro Pro Pro His Gly Ala Arg Arg Ala Arg Ser Val Ala Ser
        195                 200                 205

Ser Leu Arg Asp Asn Asn Pro Gln Val Asp Trp Lys Asp Trp Lys Ile
        210                 215                 220

Gly Phe Gln Leu Cys Asn Gln Asn Lys Ser Asp Cys Phe Tyr Gln Thr
225                 230                 235                 240

Tyr Ser Ser Gly Val Asp Ala Val Arg Glu Trp Tyr Arg Phe His Tyr
                245                 250                 255
```

```
Ile Asn Ile Leu Ser Arg Leu Pro Glu Thr Leu Pro Ser Leu Glu Glu
            260                 265                 270

Asp Thr Leu Gly Asn Phe Ile Phe Ala Cys Arg Phe Asn Gln Val Ser
            275                 280                 285

Cys Asn Gln Ala Asn Tyr Ser His Phe His Pro Met Tyr Gly Asn
            290                 295                 300

Cys Tyr Thr Phe Asn Asp Lys Asn Asn Ser Asn Leu Trp Met Ser Ser
305                 310                 315                 320

Met Pro Gly Ile Asn Asn Gly Leu Ser Leu Met Leu Arg Ala Glu Gln
            325                 330                 335

Asn Asp Phe Ile Pro Leu Leu Ser Thr Val Thr Gly Ala Arg Val Met
            340                 345                 350

Val His Gly Gln Asp Glu Pro Ala Phe Met Asp Asp Gly Gly Phe Asn
            355                 360                 365

Leu Arg Pro Gly Val Glu Thr Ser Ile Ser Met Arg Lys Glu Thr Leu
            370                 375                 380

Asp Arg Leu Gly Gly Asp Tyr Gly Asp Cys Thr Lys Asn Gly Ser Asp
385                 390                 395                 400

Val Pro Val Glu Asn Leu Tyr Pro Ser Lys Tyr Thr Gln Gln Val Cys
            405                 410                 415

Ile His Ser Cys Phe Gln Glu Ser Met Ile Lys Glu Cys Gly Cys Ala
            420                 425                 430

Tyr Ile Phe Tyr Pro Arg Pro Gln Asn Val Glu Tyr Cys Asp Tyr Arg
            435                 440                 445

Lys His Ser Ser Trp Gly Tyr Cys Tyr Tyr Lys Leu Gln Val Asp Phe
            450                 455                 460

Ser Ser Asp His Leu Gly Cys Phe Thr Lys Cys Arg Lys Pro Cys Ser
465                 470                 475                 480

Val Thr Ser Tyr Gln Leu Ser Ala Gly Tyr Ser Arg Trp Pro Ser Val
            485                 490                 495

Thr Ser Gln Glu Trp Val Phe Gln Met Leu Ser Arg Gln Asn Asn Tyr
            500                 505                 510

Thr Val Asn Asn Lys Arg Asn Gly Val Ala Lys Val Asn Ile Phe Phe
            515                 520                 525

Lys Glu Leu Asn Tyr Lys Thr Asn Ser Glu Ser Pro Ser Val Thr Met
            530                 535                 540

Val Thr Leu Leu Ser Asn Leu Gly Ser Gln Trp Ser Leu Trp Phe Gly
545                 550                 555                 560

Ser Ser Val Leu Ser Val Val Glu Met Ala Glu Leu Val Phe Asp Leu
            565                 570                 575

Leu Val Ile Met Phe Leu Met Leu Leu Arg Arg Phe Arg Ser Arg Tyr
            580                 585                 590

Trp Ser Pro Gly Arg Gly Gly Arg Gly Ala Gln Glu Val Ala Ser Thr
            595                 600                 605

Leu Ala Ser Ser Pro Pro Ser His Phe Cys Pro His Pro Met Ser Leu
            610                 615                 620

Ser Leu Ser Gln Pro Gly Pro Ala Pro Ser Pro Ala Leu Thr Ala Pro
625                 630                 635                 640

Pro Pro Ala Tyr Ala Thr Leu Gly Pro Arg Pro Ser Pro Gly Gly Ser
            645                 650                 655

Ala Gly Ala Ser Ser Ser Thr Cys Pro Leu Gly Gly Pro
            660                 665
```

<210> SEQ ID NO 5
<211> LENGTH: 1923
<212> TYPE: DNA
<213> ORGANISM: Homo sapiens

<400> SEQUENCE: 5

| | | | | | | |
|---|---|---|---|---|---|---|
| atgcacgtga | agaagtacct | gctgaagggc | ctgcatcggc | tgcagaaggg | ccccggctac | 60 |
| acgtacaagg | agctgctggt | gtggtactgc | gacaacacca | acaccacgg | ccccaagcgc | 120 |
| atcatctgtg | aggggcccaa | gaagaaagcc | atgtggttcc | tgctcaccct | gctcttcgcc | 180 |
| gccctcgtct | gctggcagtg | gggcatcttc | atcaggacct | acttgagctg | ggaggtcagc | 240 |
| gtctccctct | ccgtaggctt | caagaccatg | gacttccccg | ccgtcaccat | ctgcaatgct | 300 |
| agccccttca | gtattccaa | aatcaagcat | ttgctgaagg | acctggatga | gctgatggaa | 360 |
| gctgtcctgg | agagaatcct | ggctcctgag | ctaagccatg | ccaatgccac | caggaacctg | 420 |
| aacttctcca | tctggaacca | cacaccctg | tccttattg | atgaacggaa | cccccaccac | 480 |
| cccatggtcc | ttgatctctt | tggagacaac | acacaatggc | taacaagcag | ctcagcatca | 540 |
| gaaaagatct | gtaatgccca | cgggtgcaaa | atggccatga | gactatgtag | cctcaacagg | 600 |
| acccagtgta | ccttccggaa | cttcaccagt | gctacccagg | cattgacaga | gtggtacatc | 660 |
| ctgcaggcca | ccaacatctt | tgcacaggtg | ccacagcagg | agctagtaga | tgagctac | 720 |
| cccggcgagc | agatgatcct | ggcctgccta | ttcggagctg | agccctgcaa | ctaccggaac | 780 |
| ttcacgtcca | tcttctaccc | tcactatggc | aactgttaca | tcttcaactg | gggcatgaca | 840 |
| gagaaggcac | ttccttcggc | caaccctgga | actgaattcg | gcctgaagtt | gatcctggac | 900 |
| ataggccagg | aagactacgt | ccccttcctt | gcgtccacgg | ccggggtcag | gctgatgctt | 960 |
| cacgagcaga | ggtcataccc | cttcatcaga | gatgagggca | tctacgccat | gtcgggggaca | 1020 |
| gagacgtcca | tcggggtact | cgtggacaag | cttcagcgca | tggggagcc | ctacagcccg | 1080 |
| tgcaccgtga | atggttctga | ggtccccgtc | caaaacttct | acagtgacta | caacacgacc | 1140 |
| tactccatcc | aggcctgtct | tcgctcctgc | ttccaagacc | acatgatccg | taactgcaac | 1200 |
| tgtggccact | acctgtaccc | actgccccgt | ggggagaaat | actgcaacaa | ccggacttc | 1260 |
| ccagactggg | cccattgcta | ctcagatcta | cagatgagcg | tggcgcagag | agagacctgc | 1320 |
| attggcatgt | gcaaggagtc | ctgcaatgac | acccagtaca | agatgaccat | ctccatggct | 1380 |
| gactggcctt | ctgaggcctc | cgaggactgg | attttccacg | tcttgtctca | ggagcgggac | 1440 |
| caaagcacca | atatcaccct | gagcaggaag | ggaattgtca | agctcaacat | ctacttccaa | 1500 |
| gaatttaact | atcgcaccat | tgaagaatca | gcagccaata | acatcgtctg | gctgctctcg | 1560 |
| aatctgggtg | gccagtttgg | cttctggatg | ggggctctg | tgctgtgcct | catcgagttt | 1620 |
| ggggagatca | tcatcgactt | tgtgtggatc | accatcatca | gctggtggc | cttggccaag | 1680 |
| agcctacggc | agcggcgagc | ccaagccagc | tacgctggcc | caccgcccac | cgtggccgag | 1740 |
| ctggtggagg | cccacaccaa | cttttggctt | cagcctgaca | cggcccccg | cagccccaac | 1800 |
| actgggccct | accccagtga | gcaggccctg | cccatcccag | gcacccccgcc | ccccaactat | 1860 |
| gactccctgc | gtctgcagcc | gctggacgtc | atcgagtctg | acagtgaggg | tgatgccatc | 1920 |
| taa | | | | | | 1923 |

<210> SEQ ID NO 6
<211> LENGTH: 640
<212> TYPE: PRT
<213> ORGANISM: Homo sapiens

<400> SEQUENCE: 6

```
Met His Val Lys Lys Tyr Leu Leu Lys Gly Leu His Arg Leu Gln Lys
1               5                   10                  15

Gly Pro Gly Tyr Thr Tyr Lys Glu Leu Leu Val Trp Tyr Cys Asp Asn
            20                  25                  30

Thr Asn Thr His Gly Pro Lys Arg Ile Ile Cys Glu Gly Pro Lys Lys
        35                  40                  45

Lys Ala Met Trp Phe Leu Leu Thr Leu Leu Phe Ala Ala Leu Val Cys
    50                  55                  60

Trp Gln Trp Gly Ile Phe Ile Arg Thr Tyr Leu Ser Trp Glu Val Ser
65              70                  75                  80

Val Ser Leu Ser Val Gly Phe Lys Thr Met Asp Phe Pro Ala Val Thr
                85                  90                  95

Ile Cys Asn Ala Ser Pro Phe Lys Tyr Ser Lys Ile Lys His Leu Leu
            100                 105                 110

Lys Asp Leu Asp Glu Leu Met Glu Ala Val Leu Glu Arg Ile Leu Ala
        115                 120                 125

Pro Glu Leu Ser His Ala Asn Ala Thr Arg Asn Leu Asn Phe Ser Ile
130                 135                 140

Trp Asn His Thr Pro Leu Val Leu Ile Asp Glu Arg Asn Pro His His
145                 150                 155                 160

Pro Met Val Leu Asp Leu Phe Gly Asp Asn His Asn Gly Leu Thr Ser
                165                 170                 175

Ser Ser Ala Ser Glu Lys Ile Cys Asn Ala His Gly Cys Lys Met Ala
            180                 185                 190

Met Arg Leu Cys Ser Leu Asn Arg Thr Gln Cys Thr Phe Arg Asn Phe
        195                 200                 205

Thr Ser Ala Thr Gln Ala Leu Thr Glu Trp Tyr Ile Leu Gln Ala Thr
210                 215                 220

Asn Ile Phe Ala Gln Val Pro Gln Gln Glu Leu Val Glu Met Ser Tyr
225                 230                 235                 240

Pro Gly Glu Gln Met Ile Leu Ala Cys Leu Phe Gly Ala Glu Pro Cys
                245                 250                 255

Asn Tyr Arg Asn Phe Thr Ser Ile Phe Tyr Pro His Tyr Gly Asn Cys
            260                 265                 270

Tyr Ile Phe Asn Trp Gly Met Thr Glu Lys Ala Leu Pro Ser Ala Asn
        275                 280                 285

Pro Gly Thr Glu Phe Gly Leu Lys Leu Ile Leu Asp Ile Gly Gln Glu
290                 295                 300

Asp Tyr Val Pro Phe Leu Ala Ser Thr Ala Gly Val Arg Leu Met Leu
305                 310                 315                 320

His Glu Gln Arg Ser Tyr Pro Phe Ile Arg Asp Glu Gly Ile Tyr Ala
                325                 330                 335

Met Ser Gly Thr Glu Thr Ser Ile Gly Val Leu Val Asp Lys Leu Gln
            340                 345                 350

Arg Met Gly Glu Pro Tyr Ser Pro Cys Thr Val Asn Gly Ser Glu Val
        355                 360                 365

Pro Val Gln Asn Phe Tyr Ser Asp Tyr Asn Thr Thr Tyr Ser Ile Gln
370                 375                 380

Ala Cys Leu Arg Ser Cys Phe Gln Asp His Met Ile Arg Asn Cys Asn
385                 390                 395                 400

Cys Gly His Tyr Leu Tyr Pro Leu Pro Arg Gly Glu Lys Tyr Cys Asn
```

```
                    405                 410                 415
Asn Arg Asp Phe Pro Asp Trp Ala His Cys Tyr Ser Asp Leu Gln Met
            420                 425                 430

Ser Val Ala Gln Arg Glu Thr Cys Ile Gly Met Cys Lys Glu Ser Cys
            435                 440                 445

Asn Asp Thr Gln Tyr Lys Met Thr Ile Ser Met Ala Asp Trp Pro Ser
    450                 455                 460

Glu Ala Ser Glu Asp Trp Ile Phe His Val Leu Ser Gln Glu Arg Asp
465                 470                 475                 480

Gln Ser Thr Asn Ile Thr Leu Ser Arg Lys Gly Ile Val Lys Leu Asn
                485                 490                 495

Ile Tyr Phe Gln Glu Phe Asn Tyr Arg Thr Ile Glu Glu Ser Ala Ala
                500                 505                 510

Asn Asn Ile Val Trp Leu Leu Ser Asn Leu Gly Gly Gln Phe Gly Phe
            515                 520                 525

Trp Met Gly Gly Ser Val Leu Cys Leu Ile Glu Phe Gly Glu Ile Ile
    530                 535                 540

Ile Asp Phe Val Trp Ile Thr Ile Ile Lys Leu Val Ala Leu Ala Lys
545                 550                 555                 560

Ser Leu Arg Gln Arg Arg Ala Gln Ala Ser Tyr Ala Gly Pro Pro Pro
                565                 570                 575

Thr Val Ala Glu Leu Val Glu Ala His Thr Asn Phe Gly Phe Gln Pro
            580                 585                 590

Asp Thr Ala Pro Arg Ser Pro Asn Thr Gly Pro Tyr Pro Ser Glu Gln
            595                 600                 605

Ala Leu Pro Ile Pro Gly Thr Pro Pro Asn Tyr Asp Ser Leu Arg
            610                 615                 620

Leu Gln Pro Leu Asp Val Ile Glu Ser Asp Ser Glu Gly Asp Ala Ile
625                 630                 635                 640

<210> SEQ ID NO 7
<211> LENGTH: 1950
<212> TYPE: DNA
<213> ORGANISM: Homo sapiens

<400> SEQUENCE: 7
atggcacccg agagaagat  caaagccaaa atcaagaaga atctgcccgt gacgggccct      60
caggcgccga ccattaaaga gctgatgcgg tggtactgcc tcaacaccaa cacccatggc     120
tgtcgccgca tcgtggtgtc ccgcggccgt ctgcgccgcc tcctctggat cgggttcaca     180
ctgactgccg tggccctcat cctctggcag tgcgccctcc tcgtcttctc cttctatact     240
gtctcagttt ccatcaaagt ccacttccgg aagctggatt ttcctgcagt caccatctgc     300
aacatcaacc cctacaagta cagcaccgtt cgccaccttc tagctgactt ggaacaggag     360
accagagagg ccctgaagtc cctgtatggc tttccagagt cccggaagcg ccgagaggcg     420
gagtcctgga actccgtctc agagggaaag cagcctagat tctcccaccg gattccgctg     480
ctgatctttg atcaggatga aagggcaag gccagggact tcttcacagg gaggaagcgg     540
aaagtcggcg gtagcatcat tcacaaggct tcaaatgtca tgcacatcga gtccaagcaa     600
gtggtgggat tccaactgtg ctcaaatgac acctccgact gtgccaccta caccttcagc     660
tcgggaatca atgccattca ggagtggtat aagctacact acatgaacat catggcacag     720
gtgcctctgg agaagaaaat caacatgagc tattctgctg aggagctgct ggtgacctgc     780
ttctttgatg gagtgtcctg tgatgccagg aatttcacgc ttttccacca cccgatgcat     840
```

-continued

```
gggaattgct atactttcaa caacagagaa aatgagacca ttctcagcac ctccatgggg    900
ggcagcgaat atgggctgca agtcattttg tacataaacg aagaggaata caacccattc    960
ctcgtgtcct ccactggagc taaggtgatc atccatcggc aggatgagta tcccttcgtc   1020
gaagatgtgg gaacagagat tgagacagca atggtcacct ctataggaat gcacctgaca   1080
gagtccttca agctgagtga gccctacagt cagtgcacgg aggacgggag tgacgtgcca   1140
atcaggaaca tctacaacgc tgcctactcg ctccagatct gccttcattc atgcttccag   1200
acaaagatgg tggagaaatg tgggtgtgcc cagtacagcc agcctctacc tcctgcagcc   1260
aactactgca actaccagca gcaccccaac tggatgtatt gttactacca actgcatcga   1320
gcctttgtcc aggaagagct gggctgccag tctgtgtgca aggaagcctg cagctttaaa   1380
gagtggacac taaccacaag cctggcacaa tggccatctg tggtttcgga agtggttg    1440
ctgcctgttc tcacttggga ccaaggccgg caagtaaaca aaaagctcaa caagacagac   1500
ttggccaaac tcttgatatt ctacaaagac ctgaaccaga gatccatcat ggagagccca   1560
gccaacagta ttgagatgct tctgtccaac ttcggtggcc agctgggcct gtggatgagc   1620
tgctctgttg tctgcgtcat cgagatcatc gaggtcttct tcattgactt cttctctatc   1680
attgcccgcc gccagtggca gaaagccaag gagtggtggg cctggaaaca ggctccccca   1740
tgtccagaag ctccccgtag cccacagggc caggacaatc cagccctgga tatagacgat   1800
gacctaccca ctttcaactc tgctttgcac ctgcctccag ccctaggaac ccaagtgccc   1860
ggcacaccgc cccccaaata caataccttg cgcttggaga gggcctttc caaccagctc   1920
acagataccc agatgctaga tgagctctga                                    1950
```

<210> SEQ ID NO 8
<211> LENGTH: 649
<212> TYPE: PRT
<213> ORGANISM: Homo sapiens

<400> SEQUENCE: 8

```
Met Ala Pro Gly Glu Lys Ile Lys Ala Lys Ile Lys Lys Asn Leu Pro
1               5                   10                  15

Val Thr Gly Pro Gln Ala Pro Thr Ile Lys Glu Leu Met Arg Trp Tyr
            20                  25                  30

Cys Leu Asn Thr Asn Thr His Gly Cys Arg Arg Ile Val Val Ser Arg
        35                  40                  45

Gly Arg Leu Arg Arg Leu Leu Trp Ile Gly Phe Thr Leu Thr Ala Val
    50                  55                  60

Ala Leu Ile Leu Trp Gln Cys Ala Leu Leu Val Phe Ser Phe Tyr Thr
65                  70                  75                  80

Val Ser Val Ser Ile Lys Val His Phe Arg Lys Leu Asp Phe Pro Ala
                85                  90                  95

Val Thr Ile Cys Asn Ile Asn Pro Tyr Lys Tyr Ser Thr Val Arg His
            100                 105                 110

Leu Leu Ala Asp Leu Glu Gln Glu Thr Arg Glu Ala Leu Lys Ser Leu
        115                 120                 125

Tyr Gly Phe Pro Glu Ser Arg Lys Arg Glu Ala Glu Ser Trp Asn
    130                 135                 140

Ser Val Ser Glu Gly Lys Gln Pro Arg Phe Ser His Arg Ile Pro Leu
145                 150                 155                 160

Leu Ile Phe Asp Gln Asp Glu Lys Gly Lys Ala Arg Asp Phe Phe Thr
                165                 170                 175
```

Gly Arg Lys Arg Lys Val Gly Ser Ile Ile His Lys Ala Ser Asn
            180                 185                 190

Val Met His Ile Glu Ser Lys Gln Val Val Gly Phe Gln Leu Cys Ser
            195                 200                 205

Asn Asp Thr Ser Asp Cys Ala Thr Tyr Thr Phe Ser Ser Gly Ile Asn
            210                 215                 220

Ala Ile Gln Glu Trp Tyr Lys Leu His Tyr Met Asn Ile Met Ala Gln
225                 230                 235                 240

Val Pro Leu Glu Lys Lys Ile Asn Met Ser Tyr Ser Ala Glu Glu Leu
            245                 250                 255

Leu Val Thr Cys Phe Phe Asp Gly Val Ser Cys Asp Ala Arg Asn Phe
            260                 265                 270

Thr Leu Phe His His Pro Met His Gly Asn Cys Tyr Thr Phe Asn Asn
            275                 280                 285

Arg Glu Asn Glu Thr Ile Leu Ser Thr Ser Met Gly Gly Ser Glu Tyr
            290                 295                 300

Gly Leu Gln Val Ile Leu Tyr Ile Asn Glu Glu Tyr Asn Pro Phe
305                 310                 315                 320

Leu Val Ser Ser Thr Gly Ala Lys Val Ile His Arg Gln Asp Glu
            325                 330                 335

Tyr Pro Phe Val Glu Asp Val Gly Thr Glu Ile Glu Thr Ala Met Val
            340                 345                 350

Thr Ser Ile Gly Met His Leu Thr Glu Ser Phe Lys Leu Ser Glu Pro
            355                 360                 365

Tyr Ser Gln Cys Thr Glu Asp Gly Ser Asp Val Pro Ile Arg Asn Ile
            370                 375                 380

Tyr Asn Ala Ala Tyr Ser Leu Gln Ile Cys Leu His Ser Cys Phe Gln
385                 390                 395                 400

Thr Lys Met Val Glu Lys Cys Gly Cys Ala Gln Tyr Ser Gln Pro Leu
            405                 410                 415

Pro Pro Ala Ala Asn Tyr Cys Asn Tyr Gln Gln His Pro Asn Trp Met
            420                 425                 430

Tyr Cys Tyr Tyr Gln Leu His Arg Ala Phe Val Gln Glu Glu Leu Gly
            435                 440                 445

Cys Gln Ser Val Cys Lys Glu Ala Cys Ser Phe Lys Glu Trp Thr Leu
            450                 455                 460

Thr Thr Ser Leu Ala Gln Trp Pro Ser Val Val Ser Glu Lys Trp Leu
465                 470                 475                 480

Leu Pro Val Leu Thr Trp Asp Gln Gly Arg Gln Val Asn Lys Lys Leu
            485                 490                 495

Asn Lys Thr Asp Leu Ala Lys Leu Leu Ile Phe Tyr Lys Asp Leu Asn
            500                 505                 510

Gln Arg Ser Ile Met Glu Ser Pro Ala Asn Ser Ile Glu Met Leu Leu
            515                 520                 525

Ser Asn Phe Gly Gly Gln Leu Gly Leu Trp Met Ser Cys Ser Val Val
            530                 535                 540

Cys Val Ile Glu Ile Ile Glu Val Phe Phe Ile Asp Phe Phe Ser Ile
545                 550                 555                 560

Ile Ala Arg Arg Gln Trp Gln Lys Ala Lys Glu Trp Trp Ala Trp Lys
            565                 570                 575

Gln Ala Pro Pro Cys Pro Glu Ala Pro Arg Ser Pro Gln Gly Gln Asp
            580                 585                 590

Asn Pro Ala Leu Asp Ile Asp Asp Leu Pro Thr Phe Asn Ser Ala
        595                 600                 605

Leu His Leu Pro Pro Ala Leu Gly Thr Gln Val Pro Gly Thr Pro Pro
    610                 615                 620

Pro Lys Tyr Asn Thr Leu Arg Leu Glu Arg Ala Phe Ser Asn Gln Leu
625                 630                 635                 640

Thr Asp Thr Gln Met Leu Asp Glu Leu
            645

<210> SEQ ID NO 9
<211> LENGTH: 1917
<212> TYPE: DNA
<213> ORGANISM: Homo sapiens

<400> SEQUENCE: 9

| | | | | | |
|---|---|---|---|---|---|
| atggctgagc | accgaagcat | ggacgggaga | atggaagcag | ccacacgggg | gggctctcac | 60 |
| ctccaggctg | cagcccagac | gccccccagg | ccggggccac | catcagcacc | accaccacca | 120 |
| cccaaggagg | ggcaccagga | ggggctggtg | agctgcccg | cctcgttccg | ggagctgctc | 180 |
| accttcttct | gcaccaatgc | caccatccac | ggcgccatcc | gcctggtctg | ctcccgcggg | 240 |
| aaccgcctca | agacgacgtc | ctggggggctg | ctgtccctgg | gagccctggt | cgcgtctgc | 300 |
| tggcagctgg | ggctcctctt | tgagcgtcac | tggcaccgcc | cggtcctcat | ggccgtctct | 360 |
| gtgcactcgg | agcgcaagct | gctcccgctg | gtcaccctgt | gtgacgggaa | cccacgtcgg | 420 |
| ccgagtccgg | tcctccgcca | tctggagctg | ctggacgagt | ttgccaggga | gaacattgac | 480 |
| tccctgtaca | acgtcaacct | cagcaaaggc | agagccgccc | tctccgccac | tgtccccgc | 540 |
| cacgagcccc | ccttccacct | ggaccggag | atccgtctgc | agaggctgag | ccactcgggc | 600 |
| agccgggtca | gagtggggtt | cagactgtgc | aacagcacgg | gcgcgactg | cttttaccga | 660 |
| ggctacacgt | caggcgtggc | ggctgtccag | gactggtacc | acttccacta | tgtggatatc | 720 |
| ctggccctgc | tgcccgcggc | atgggaggac | agccacggga | gccaggacgg | ccacttcgtc | 780 |
| ctctcctgca | gttacgatgg | cctggactgc | caggcccgac | agttccggac | cttccaccac | 840 |
| cccacctacg | gcagctgcta | cacggtcgat | ggcgtctgga | cagctcagcg | ccccggcatc | 900 |
| acccacggag | tcggcctggt | cctcagggtt | gagcagcagc | ctcacctccc | tctgctgtcc | 960 |
| acgctggccg | catcagggt | catggttcac | ggccgtaacc | acacgccctt | cctggggcac | 1020 |
| cacagcttca | gcgtccggcc | aggacggag | gccaccatca | gcatccgaga | ggacgaggtg | 1080 |
| caccggctcg | ggagcccta | cggccactgc | accgccggcg | gggaaggcgt | ggaggtggag | 1140 |
| ctgctacaca | acacctccta | caccaggcag | gcctgcctgg | tgtcctgctt | ccagcagctg | 1200 |
| atggtggaga | cctgctcctg | tggctactac | ctccacccctc | tgccggcggg | ggctgagtac | 1260 |
| tgcagctctg | cccggcaccc | tgcctgggga | cactgcttct | accgcctcta | ccaggacctg | 1320 |
| gagacccacc | ggctcccctg | tacctcccgc | tgccccaggc | cctgcaggga | gtctgcattc | 1380 |
| aagctctcca | ctgggacctc | caggtggcct | tccgccaagt | cagctggatg | gactctggcc | 1440 |
| acgctaggtg | aacaggggct | gccgcatcag | agccacagac | agaggagcag | cctggccaaa | 1500 |
| atcaacatcg | tctaccagga | gctcaactac | cgctcagtgg | aggaggcgcc | cgtgtactcg | 1560 |
| gtgccgcagc | tgctctccgc | catgggcagc | ctctacagcc | tgtggtttgg | ggcctccgtc | 1620 |
| ctctcccctcc | tggagctcct | ggagctgctg | ctcgatgctt | ctgccctcac | cctggtgcta | 1680 |
| ggcggccgcc | ggctccgcag | ggcgtggttc | tcctggccca | gagccagccc | tgcctcaggg | 1740 |
| gcgtccagca | tcaagccaga | ggccagtcag | atgccccgc | ctgcaggcgg | cacgtcagat | 1800 |

```
gacccggagc ccagcgggcc tcatctccca cgggtgatgc ttccagggg tctggcggga    1860 gtctcagccg aagagagctg ggctgggccc cagccccttg agactctgga cacctga      1917
```

<210> SEQ ID NO 10
<211> LENGTH: 638
<212> TYPE: PRT
<213> ORGANISM: Homo sapiens

<400> SEQUENCE: 10

| Met | Ala | Glu | His | Arg | Ser | Met | Asp | Gly | Arg | Met | Glu | Ala | Ala | Thr | Arg |
|---|---|---|---|---|---|---|---|---|---|---|---|---|---|---|---|
| 1 | | | | 5 | | | | | 10 | | | | | 15 | |

| Gly | Gly | Ser | His | Leu | Gln | Ala | Ala | Ala | Gln | Thr | Pro | Pro | Arg | Pro | Gly |
|---|---|---|---|---|---|---|---|---|---|---|---|---|---|---|---|
| | | | 20 | | | | | 25 | | | | | 30 | | |

| Pro | Pro | Ser | Ala | Pro | Pro | Pro | Lys | Glu | Gly | His | Gln | Glu | Gly |
|---|---|---|---|---|---|---|---|---|---|---|---|---|---|
| | | 35 | | | | 40 | | | | 45 | | | |

| Leu | Val | Glu | Leu | Pro | Ala | Ser | Phe | Arg | Glu | Leu | Leu | Thr | Phe | Phe | Cys |
| 50 | | | | | 55 | | | | | 60 | | | | | |

| Thr | Asn | Ala | Thr | Ile | His | Gly | Ala | Ile | Arg | Leu | Val | Cys | Ser | Arg | Gly |
| 65 | | | | 70 | | | | | 75 | | | | | 80 | |

| Asn | Arg | Leu | Lys | Thr | Thr | Ser | Trp | Gly | Leu | Ser | Leu | Gly | Ala | Leu |
| | | | | 85 | | | | 90 | | | | | 95 | |

| Val | Ala | Leu | Cys | Trp | Gln | Leu | Gly | Leu | Leu | Phe | Glu | Arg | His | Trp | His |
| | | | 100 | | | | | 105 | | | | | 110 | | |

| Arg | Pro | Val | Leu | Met | Ala | Val | Ser | Val | His | Ser | Glu | Arg | Lys | Leu | Leu |
| | | 115 | | | | | 120 | | | | | 125 | | | |

| Pro | Leu | Val | Thr | Leu | Cys | Asp | Gly | Asn | Pro | Arg | Arg | Pro | Ser | Pro | Val |
| 130 | | | | | 135 | | | | | 140 | | | | | |

| Leu | Arg | His | Leu | Glu | Leu | Leu | Asp | Glu | Phe | Ala | Arg | Glu | Asn | Ile | Asp |
| 145 | | | | 150 | | | | | 155 | | | | | 160 | |

| Ser | Leu | Tyr | Asn | Val | Asn | Leu | Ser | Lys | Gly | Arg | Ala | Ala | Leu | Ser | Ala |
| | | | 165 | | | | | 170 | | | | | 175 | | |

| Thr | Val | Pro | Arg | His | Glu | Pro | Pro | Phe | His | Leu | Asp | Arg | Glu | Ile | Arg |
| | | | 180 | | | | | 185 | | | | | 190 | | |

| Leu | Gln | Arg | Leu | Ser | His | Ser | Gly | Ser | Arg | Val | Arg | Val | Gly | Phe | Arg |
| | | | | 195 | | | | | 200 | | | | | 205 | |

| Leu | Cys | Asn | Ser | Thr | Gly | Gly | Asp | Cys | Phe | Tyr | Arg | Gly | Tyr | Thr | Ser |
| | 210 | | | | | 215 | | | | | 220 | | | | |

| Gly | Val | Ala | Ala | Val | Gln | Asp | Trp | Tyr | His | Phe | His | Tyr | Val | Asp | Ile |
| 225 | | | | | 230 | | | | | 235 | | | | | 240 |

| Leu | Ala | Leu | Leu | Pro | Ala | Ala | Trp | Glu | Asp | Ser | His | Gly | Ser | Gln | Asp |
| | | | | 245 | | | | | 250 | | | | | 255 | |

| Gly | His | Phe | Val | Leu | Ser | Cys | Ser | Tyr | Asp | Gly | Leu | Asp | Cys | Gln | Ala |
| | | | | 260 | | | | | 265 | | | | | 270 | |

| Arg | Gln | Phe | Arg | Thr | Phe | His | His | Pro | Thr | Tyr | Gly | Ser | Cys | Tyr | Thr |
| | | 275 | | | | | 280 | | | | | 285 | | | |

| Val | Asp | Gly | Val | Trp | Thr | Ala | Gln | Arg | Pro | Gly | Ile | Thr | His | Gly | Val |
| | | 290 | | | | | 295 | | | | | 300 | | | |

| Gly | Leu | Val | Leu | Arg | Val | Glu | Gln | Gln | Pro | His | Leu | Pro | Leu | Leu | Ser |
| 305 | | | | | 310 | | | | | 315 | | | | | 320 |

| Thr | Leu | Ala | Gly | Ile | Arg | Val | Met | Val | His | Gly | Arg | Asn | His | Thr | Pro |
| | | | | 325 | | | | | 330 | | | | | 335 | |

| Phe | Leu | Gly | His | His | Ser | Phe | Ser | Val | Arg | Pro | Gly | Thr | Glu | Ala | Thr |
| | | | 340 | | | | | 345 | | | | | 350 | | |

-continued

```
Ile Ser Ile Arg Glu Asp Glu Val His Arg Leu Gly Ser Pro Tyr Gly
        355                 360                 365
His Cys Thr Ala Gly Gly Glu Gly Val Glu Val Glu Leu Leu His Asn
    370                 375                 380
Thr Ser Tyr Thr Arg Gln Ala Cys Leu Val Ser Cys Phe Gln Gln Leu
385                 390                 395                 400
Met Val Glu Thr Cys Ser Cys Gly Tyr Tyr Leu His Pro Leu Pro Ala
                405                 410                 415
Gly Ala Glu Tyr Cys Ser Ser Ala Arg His Pro Ala Trp Gly His Cys
                420                 425                 430
Phe Tyr Arg Leu Tyr Gln Asp Leu Glu Thr His Arg Leu Pro Cys Thr
        435                 440                 445
Ser Arg Cys Pro Arg Pro Cys Arg Glu Ser Ala Phe Lys Leu Ser Thr
    450                 455                 460
Gly Thr Ser Arg Trp Pro Ser Ala Lys Ser Ala Gly Trp Thr Leu Ala
465                 470                 475                 480
Thr Leu Gly Glu Gln Gly Leu Pro His Gln Ser His Arg Gln Arg Ser
                485                 490                 495
Ser Leu Ala Lys Ile Asn Ile Val Tyr Gln Glu Leu Asn Tyr Arg Ser
                500                 505                 510
Val Glu Glu Ala Pro Val Tyr Ser Val Pro Gln Leu Leu Ser Ala Met
            515                 520                 525
Gly Ser Leu Tyr Ser Leu Trp Phe Gly Ala Ser Val Leu Ser Leu Leu
        530                 535                 540
Glu Leu Leu Glu Leu Leu Leu Asp Ala Ser Ala Leu Thr Leu Val Leu
545                 550                 555                 560
Gly Gly Arg Arg Leu Arg Arg Ala Trp Phe Ser Trp Pro Arg Ala Ser
                565                 570                 575
Pro Ala Ser Gly Ala Ser Ser Ile Lys Pro Glu Ala Ser Gln Met Pro
                580                 585                 590
Pro Pro Ala Gly Gly Thr Ser Asp Asp Pro Glu Pro Ser Gly Pro His
            595                 600                 605
Leu Pro Arg Val Met Leu Pro Gly Val Leu Ala Gly Val Ser Ala Glu
        610                 615                 620
Glu Ser Trp Ala Gly Pro Gln Pro Leu Glu Thr Leu Asp Thr
625                 630                 635
```